United States Patent [19]
Bender et al.

[11] Patent Number: 5,522,985
[45] Date of Patent: Jun. 4, 1996

[54] SILAGE-MICROBIAL MAT SYSTEM AND METHOD

[75] Inventors: Judith A. Bender, Atlanta; Peter C. Phillips, Decatur, both of Ga.

[73] Assignee: Microbial & Aquatic Treatment Systems, Inc., Atlanta, Ga.

[21] Appl. No.: 339,548

[22] Filed: Nov. 15, 1994

Related U.S. Application Data

[63] Continuation of Ser. No. 40,628, Mar. 31, 1993, abandoned.
[51] Int. Cl.$^6$ .................................. C02F 3/10; C02F 3/34
[52] U.S. Cl. ...................... 210/150; 210/242.1; 210/602; 210/611; 47/1.4
[58] Field of Search .................................. 210/602, 610, 210/611, 615, 747, 150, 151, 170, 242.1; 435/174, 177, 288, 310, 946; 47/1.4

[56] References Cited

U.S. PATENT DOCUMENTS

| | | | |
|---|---|---|---|
| 4,165,281 | 8/1979 | Kuriyama et al. | 210/150 |
| 4,333,263 | 6/1982 | Adey | 47/1.4 |
| 4,670,149 | 6/1987 | Francis | 210/150 |
| 5,011,602 | 4/1991 | Totani et al. | 210/242.1 |
| 5,039,414 | 8/1991 | Mueller et al. | 210/610 |
| 5,096,577 | 3/1992 | Ngo et al. | 210/151 |

OTHER PUBLICATIONS

Bender, J. A., et al., "Fish Feeds from Grass Clippings," *Aquacultural Engineering*, vol. 8, pp. 1–13 (1989).

Cerniglia, C. E. et al., "Oxidation of Naphthalene by Cyanobacteria and Microalgae," *J. of Gen. Microb.*, vol. 116, pp. 495–500 (1980).

Bauer, J. E., et al., "Degradation and Mineralization of the Polycyclic Aromatic Hydrocarbons Anthracene and Naphthalene in Intertidal Marine Sediments," *Applied and Environ. Microb.*, pp. 81–90 (1985).

Bender, J. A., et al., "Lead Removal from Contaminated Water by a Mixed Microbial Ecosystem," *Wat. Sci. Tech.*, vol. 21, pp. 1661–1664 (1989).

Bender, J. A., et al., "Uptake, Transformation and Fixation of Se(VI) by a Mixed Selenium-Tolerant Ecosystem," *Water, Air and Soil Pollution*, vol. 59, pp. 359–367 (1991).

Ekpo, I., et al., "Digestibility of a Commercial Fish Feed, Wet Algae and Dried Algae by Tilapia nilotica and Silver Carp," *The Progressive Fish-Culterist*, vol. 51, pp. 83–86 (1989).

Brawley, J. P., Ph.D., *Reclamation of Metals from Water with a Silage-Microbe Ecosystem*, Mar. 1991.

*Primary Examiner*—Thomas Wyse
*Attorney, Agent, or Firm*—Jones & Askew

[57] ABSTRACT

This invention relates to remedial bacterial systems in a constructive mat including ensiliaged material, particularly constructed mixed microbial mats for specific bioremedial applications. Preferably, the constructed mixed microbial mat comprises ensiled grass clippings with a cyanobacteria and a chemotrophic bacteria.

12 Claims, 26 Drawing Sheets

5,522,985

SILAGE-MICROBIAL MAT SYSTEM AND METHOD

This is a continuation of application Ser. No. 08/040,628, filed Mar. 31, 1993, now abandoned.

BACKGROUND OF THE INVENTION

This invention relates generally to remedial bacterial systems and more particularly to a remedial bacterial system in a constructed mat including ensiliaged material.

Naturally-occurring microbial mats, composed of stratified layers of cyanobacteria and bacteria, evolved in primordial times, occupying the most inhospitable environments on earth.

More recently, mixed microbial mats, stimulated by ensiled grass clippings, were developed as an alternative fish feed. Such mats have been effective in sequestering heavy metals from contaminated water and in reducing certain metalloids to the elemental form. These first mats were cultured by simply adding ensiled grass to laboratory trays and inoculating with Oscillatoria or Anabaena. All other microbes were allowed to volunteer from the water and soil medium. No attempt was made to control the microbial colonization or to specify the types of microbes that might integrate into the mat.

SUMMARY OF THE INVENTION

This invention is directed to a constructed mixed microbial mat for specific bioremedial applications such as oil or petroleum degradation or other toxic material degradation. Such constructed mats not only have the capability of remedial action but also have high tolerance to toxic materials and remain active over extended periods of time. The invention is the discovery that a constructed microbial mat that has been innoculated with a chemotrophic bacteria has the ability to metabolically process various organic compounds, such as petroleum. The most successful bacteria found to degrade the organic compounds was Chromatium and was especially effective when a nutrient source was available in the constructed mat to provide nutrients to keep the Chromatium viable. When the mat contained ensiled vegetation with fermentative bacteria and also nitrogen-fixing bacteria, the remediation of the organic compounds by the Chromatium was sustained over extended periods of time and at elevated remediation rates. The mat is constructed by innoculating ensiled grass clippings with a cyanobacteria and a chemotrophic bacteria, and allowing the mat to develop over a several day period. The resulting mat has the capability of mineralizing various organic compounds such as the various petroleum compounds. The fermentative bacteria in the ensiled vegetation in conjunction with the cyanobacteria serve to furnish the chemotrophic bacteria with its carbon needs as well as its nitrogen/protein needs so that complete support for the chemotrophic bacteria is provided to extend its viability along with its organic mineralization capability.

These and other features and advantages of the invention will become more clearly understood upon consideration of the following detailed description and accompanying figures in which:

BRIEF DESCRIPTION OF THE FIGURES

FIG. 1 is a series of charts showing the normalized KOH readings for the various mats tested over a 28 day period.

FIG. 2 is a series of charts showing the normalized KOH readings for the various mats tested over the first 24 hour period of the experiments convened to ng/hour.

FIG. 3 is a series of charts showing the normalized KOH readings for the various mats tested over the 28 day period converted to ng/day.

FIG. 4 is a series of charts showing the cumulative percent mineralization based on unnormalized KOH readings for the various mats tested over a 28 day period.

Figure 1A:
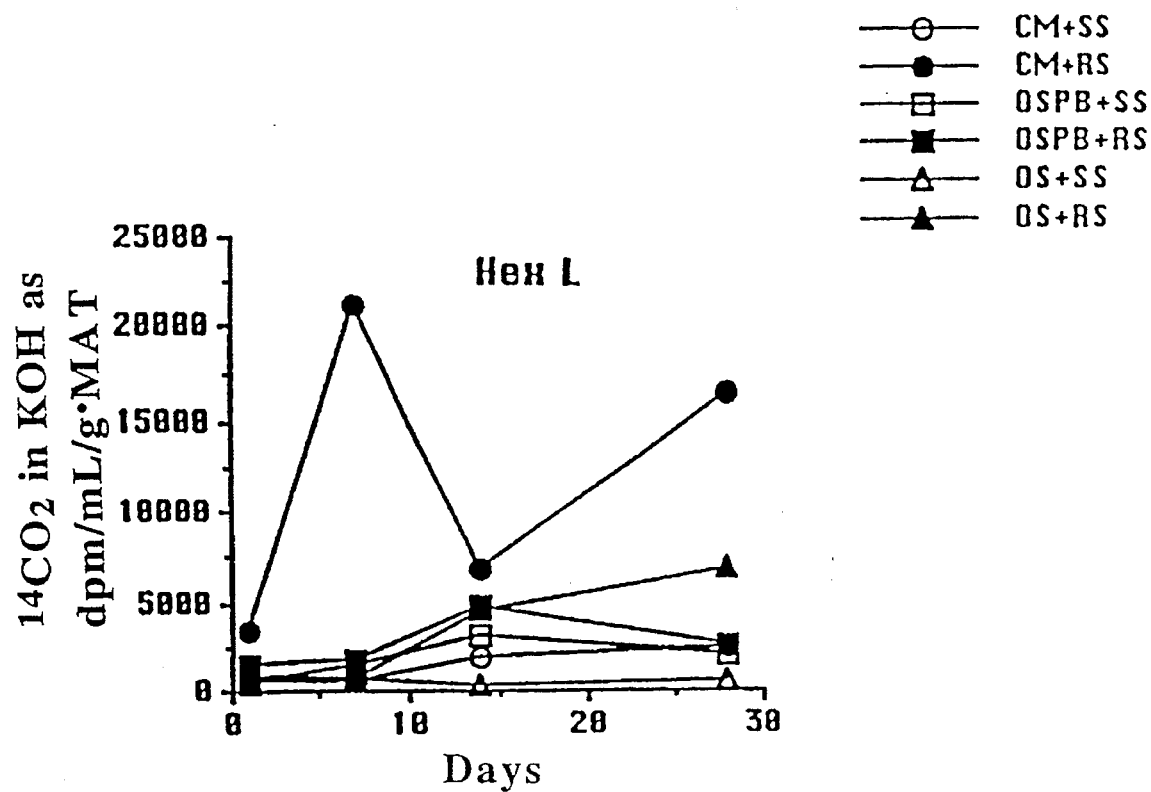
FIG. 1A shows different mat combinations with hexadecane under light conditions.
Figure 1B:
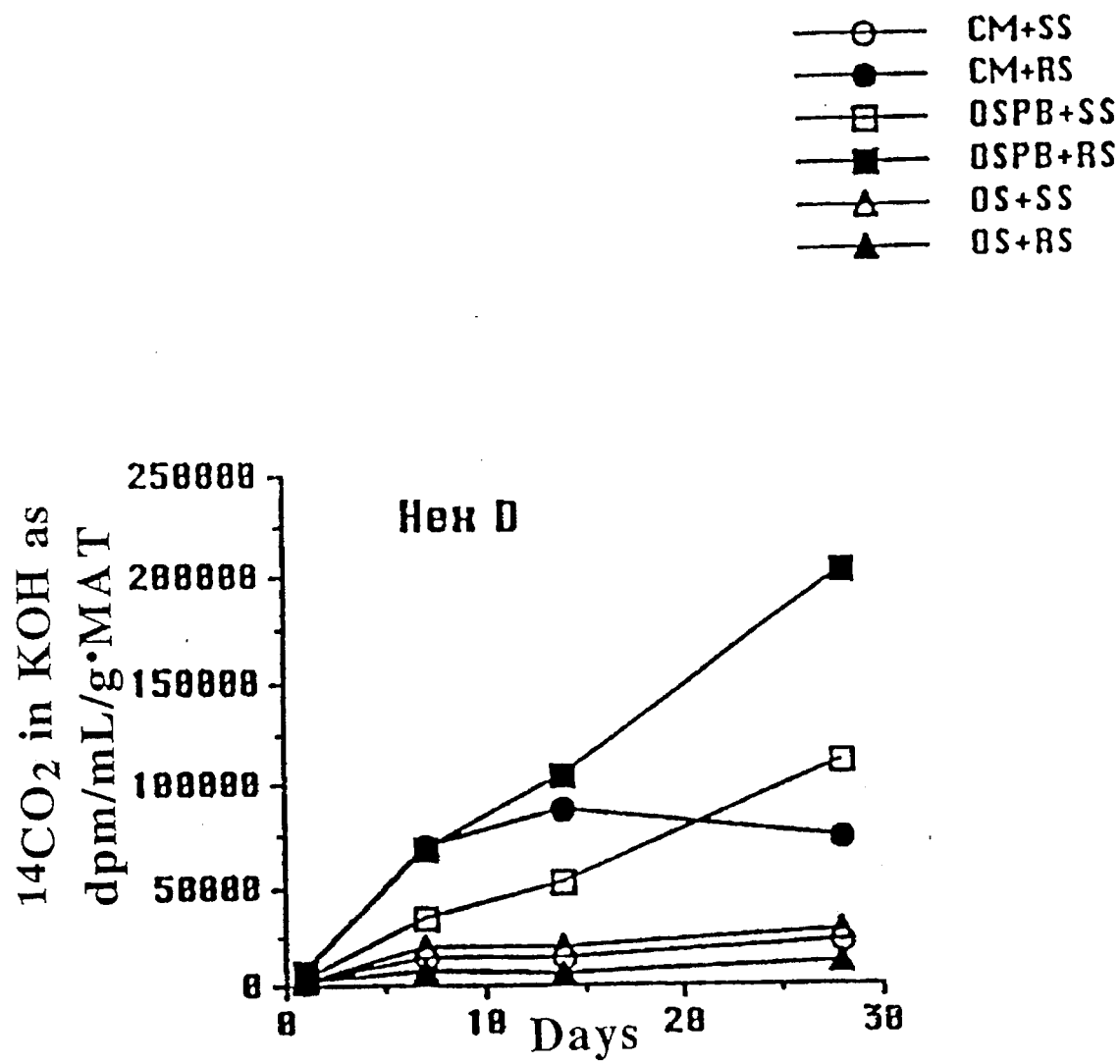
FIG. 1B shows different mat combinations with hexadecane under dark conditions.
Figure 1C:
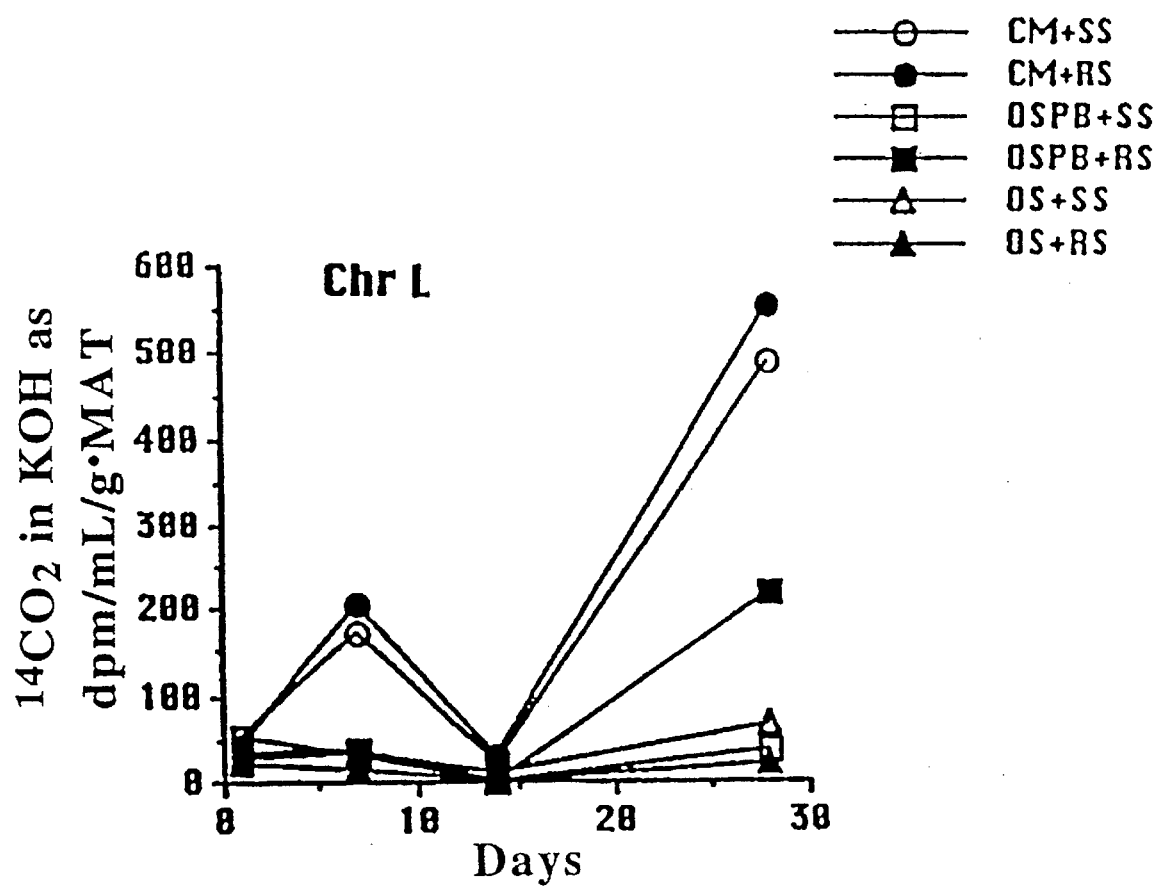
FIG. 1C shows different mat combinations with chrysene under light conditions.
Figure 1D:
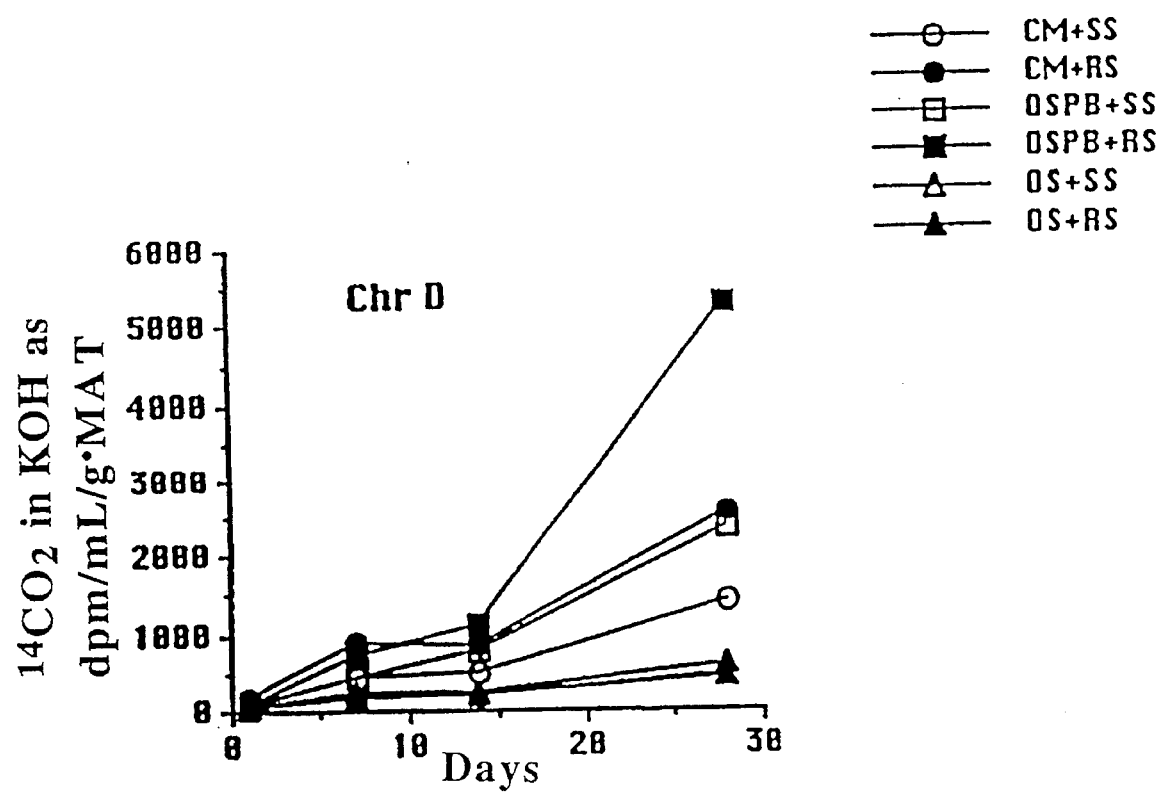
FIG. 1D shows different mat combinations with chrysene under dark conditions.
Figure 2A:
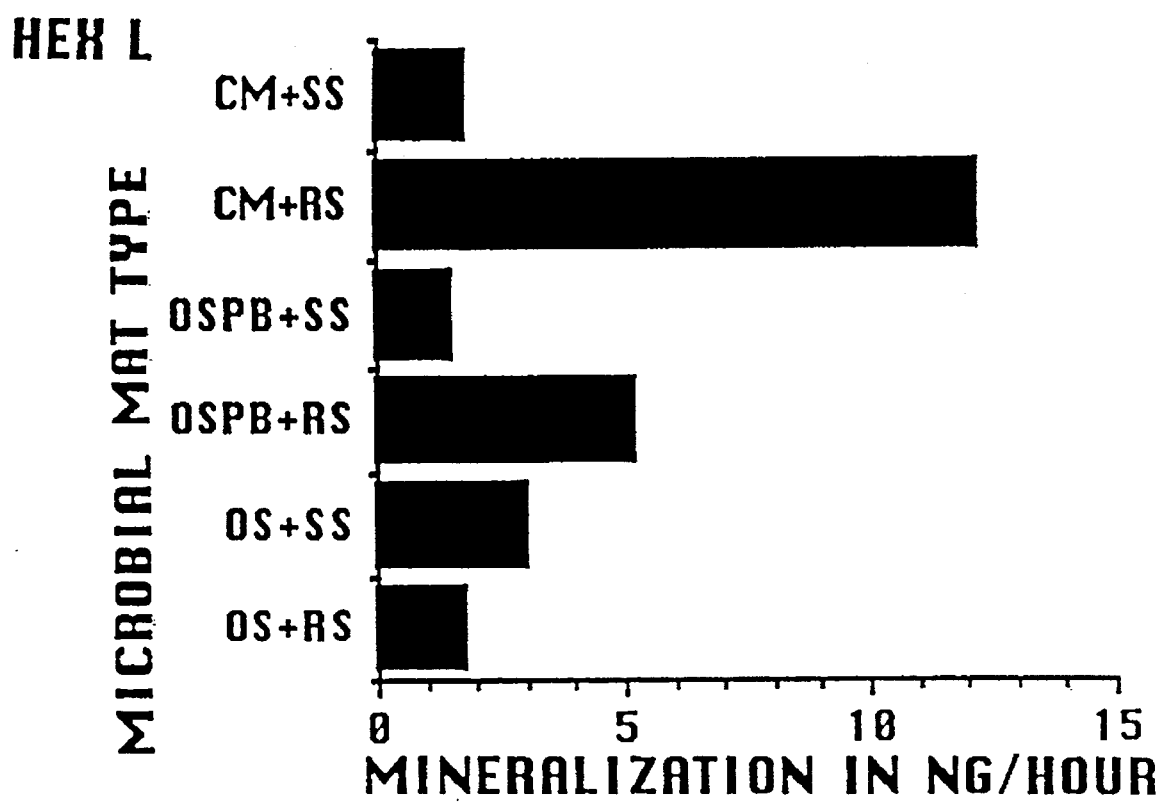
FIG. 2A shows different mat combinations with hexadecane under light conditions.
Figure 2B:
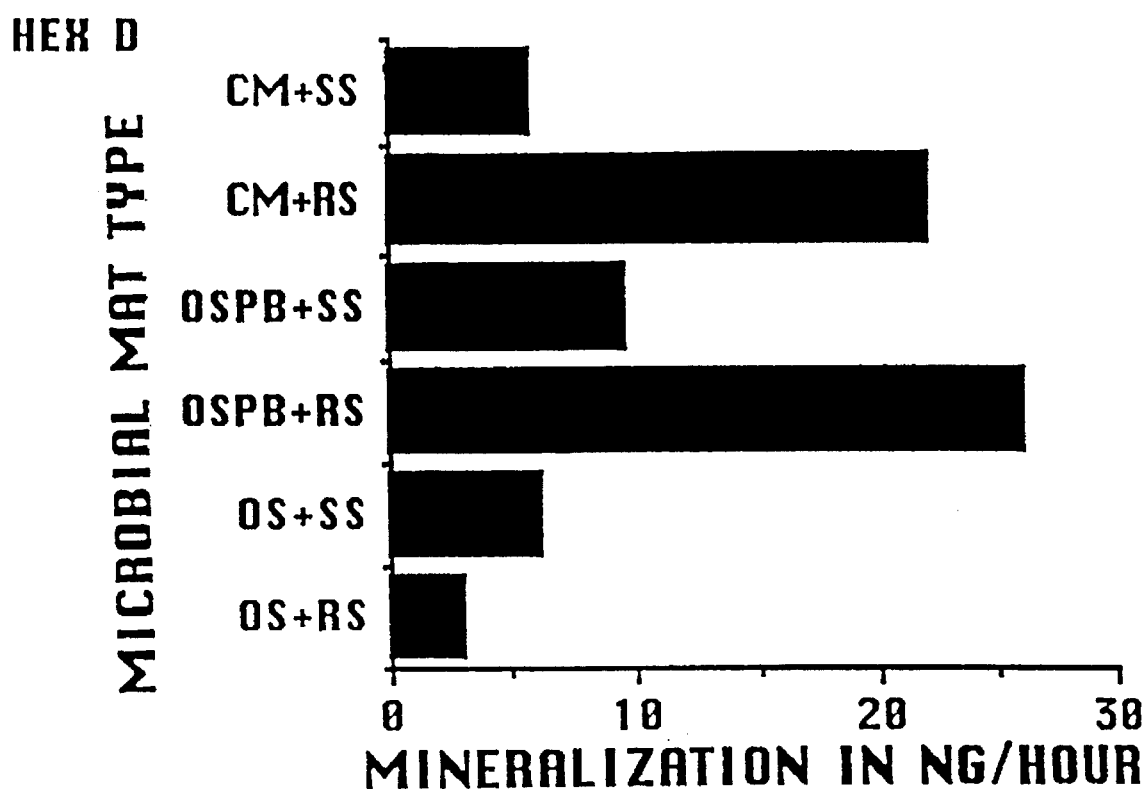
FIG. 2B shows different mat combinations with hexadecane under dark conditions.
Figure 2C:
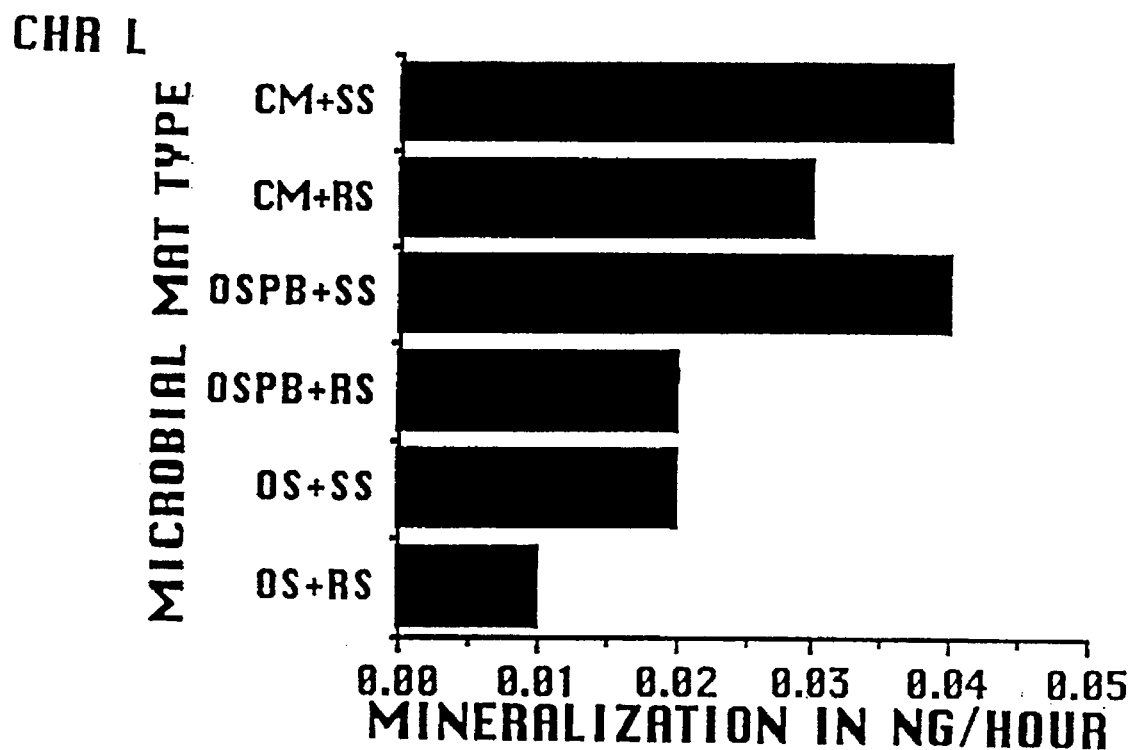
FIG. 2C shows different mat combinations with chrysene under light conditions.
Figure 2D:
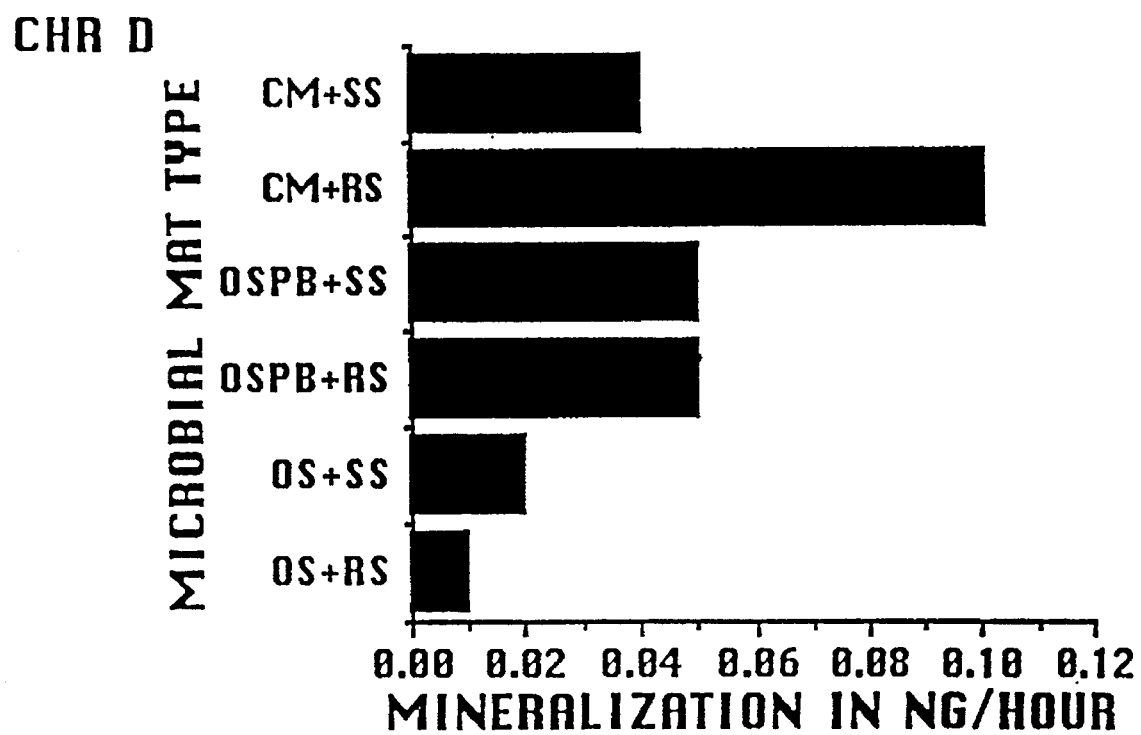
FIG. 2D shows different mat combinations with chrysene under dark conditions.
Figure 3A:
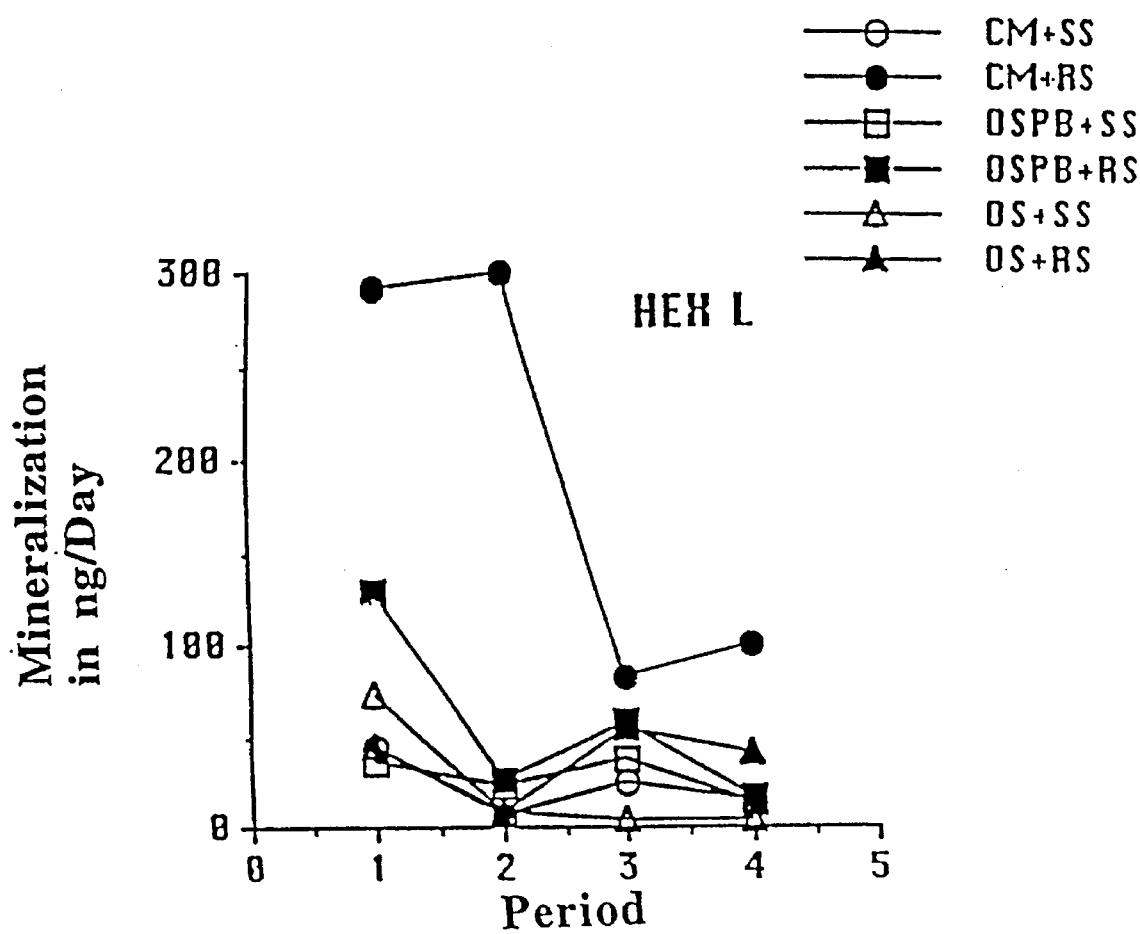
FIG. 3A shows different mat combinations with hexadecane under light conditions.
Figure 3B:
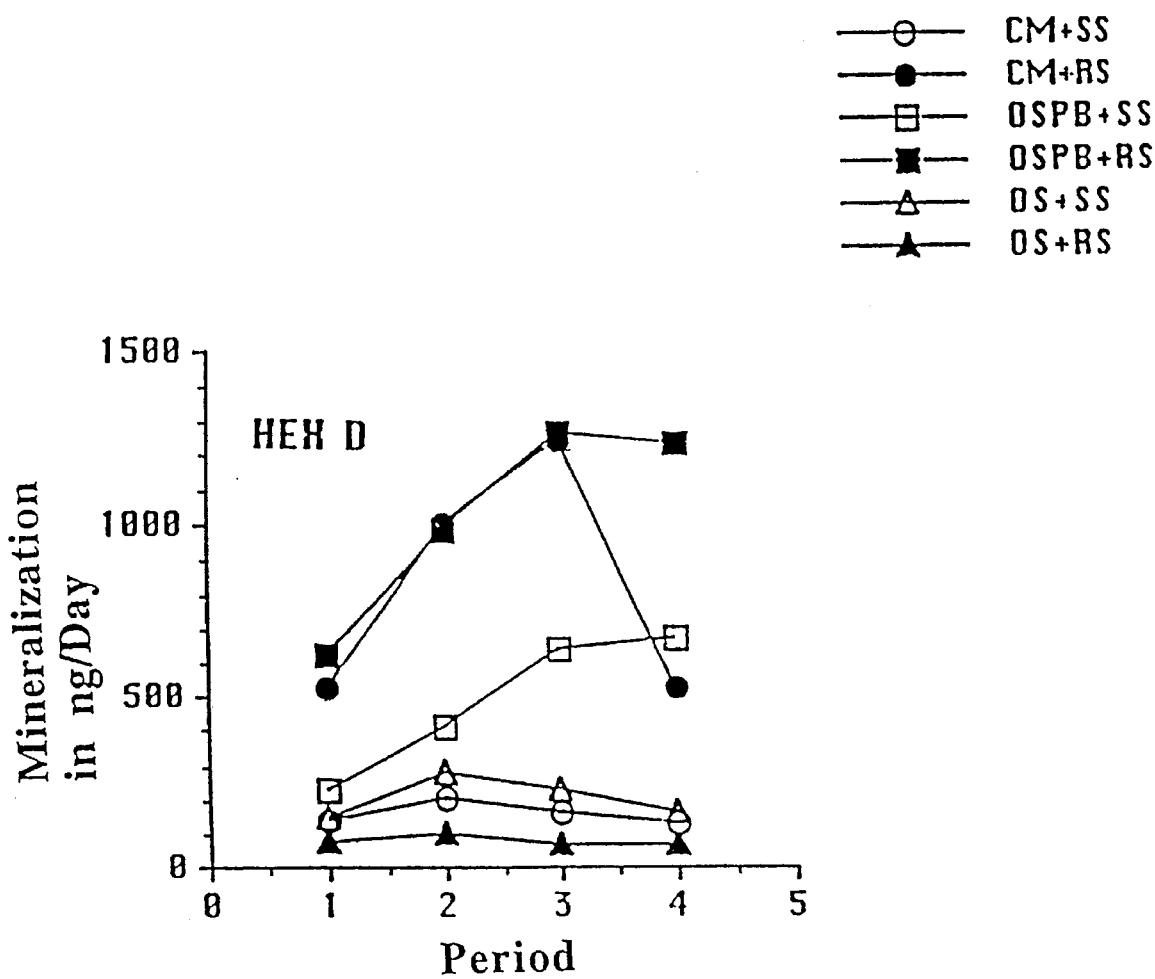
FIG. 3B shows different mat combinations with hexadecane under dark conditions.
Figure 3C:
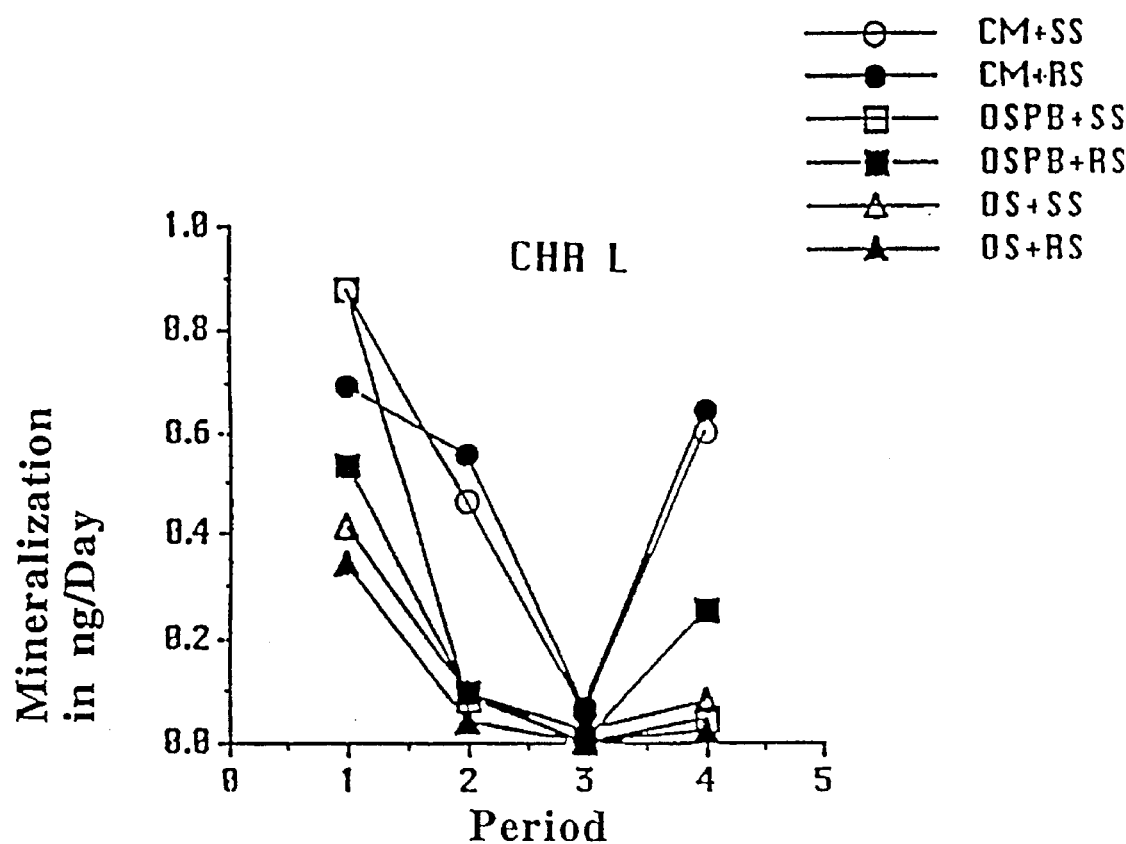
FIG. 3C shows different mat combinations with chrysene under light conditions.
Figure 3D:
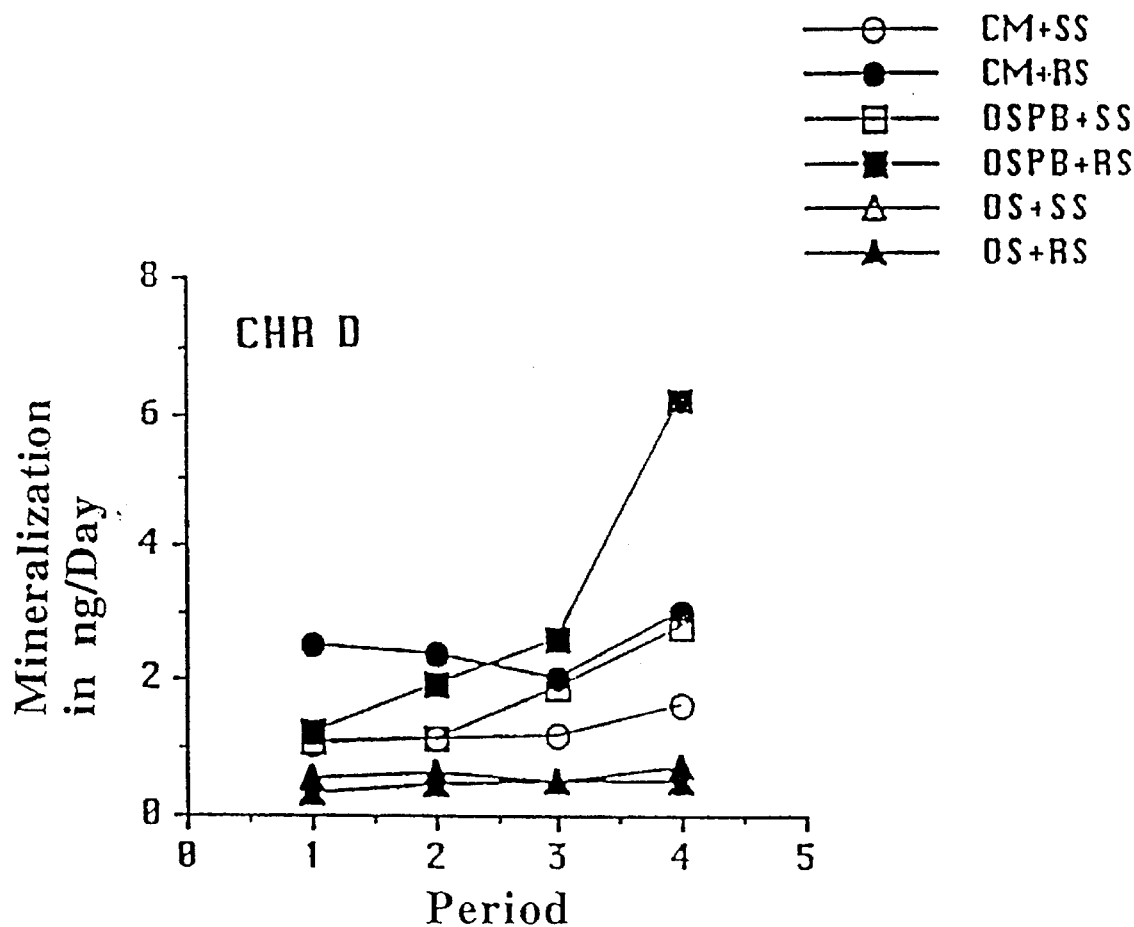
FIG. 3D shows different mat combinations with chrysene under dark conditions.
Figure 4A:
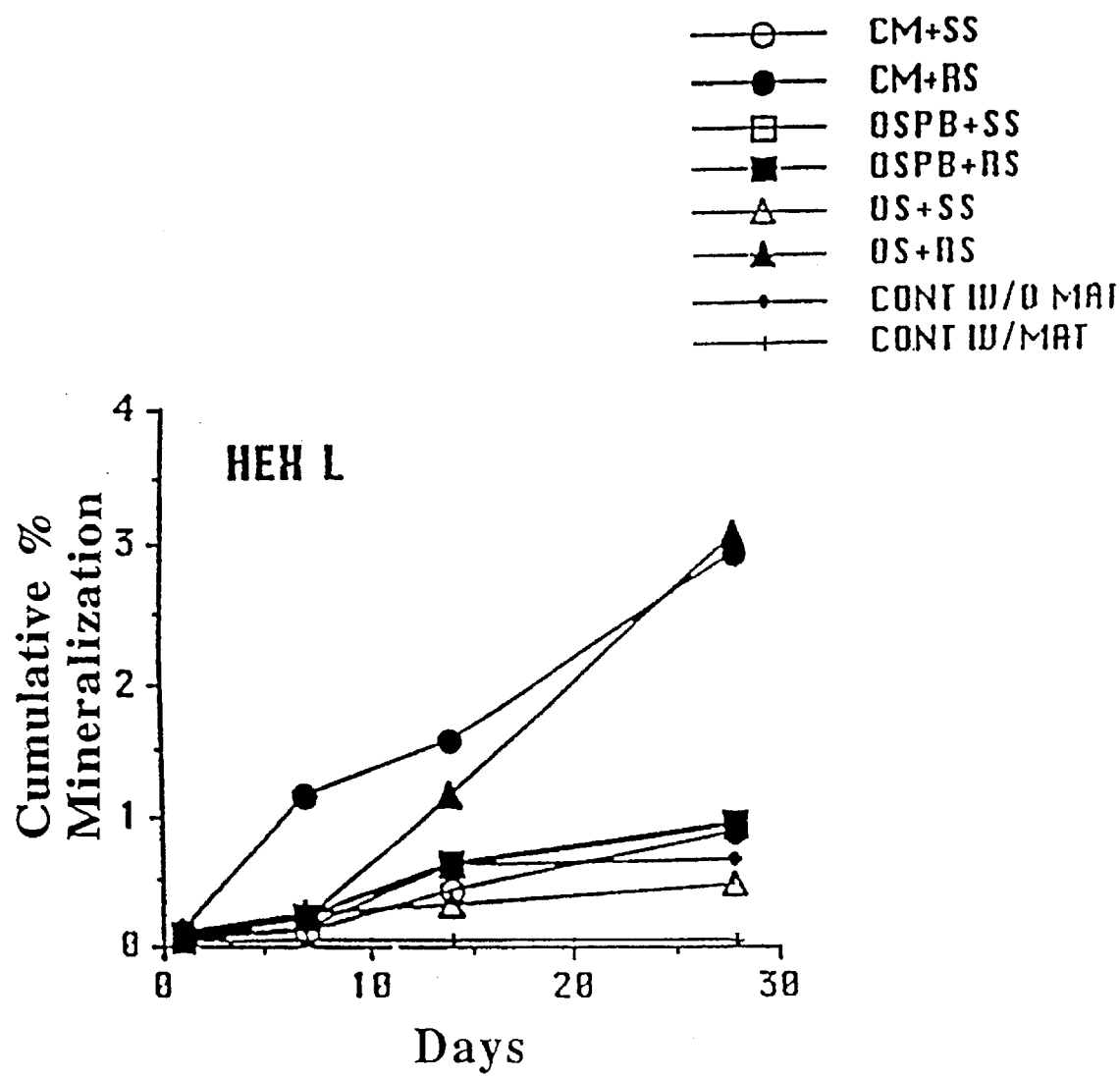
FIG. 4A shows different mat combinations with hexadecane under light conditions.
Figure 4B:
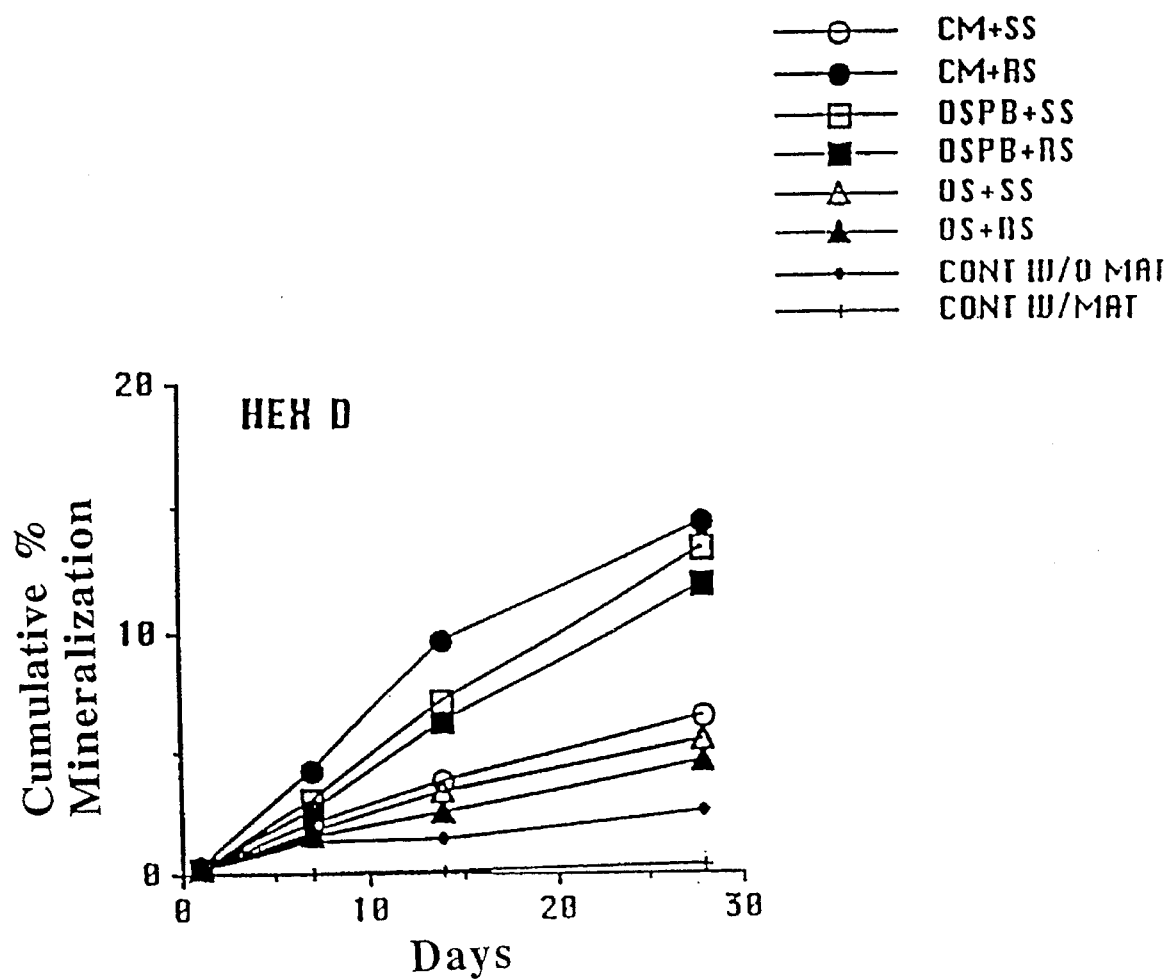
FIG. 4B shows different mat combinations with hexadecane under dark conditions.
Figure 4C:
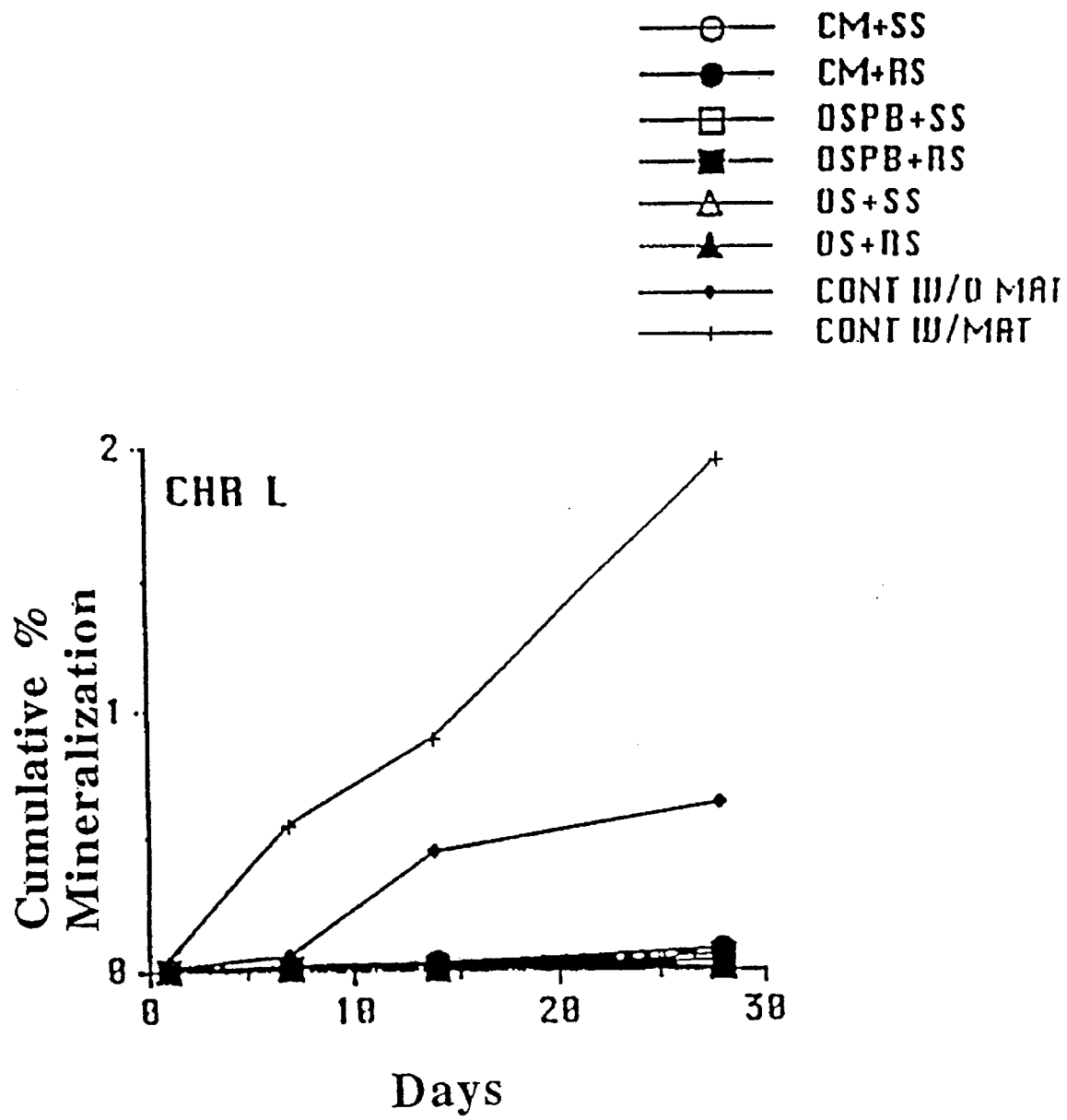
FIG. 4C shows different mat combinations with chrysene under light conditions.
Figure 4D:
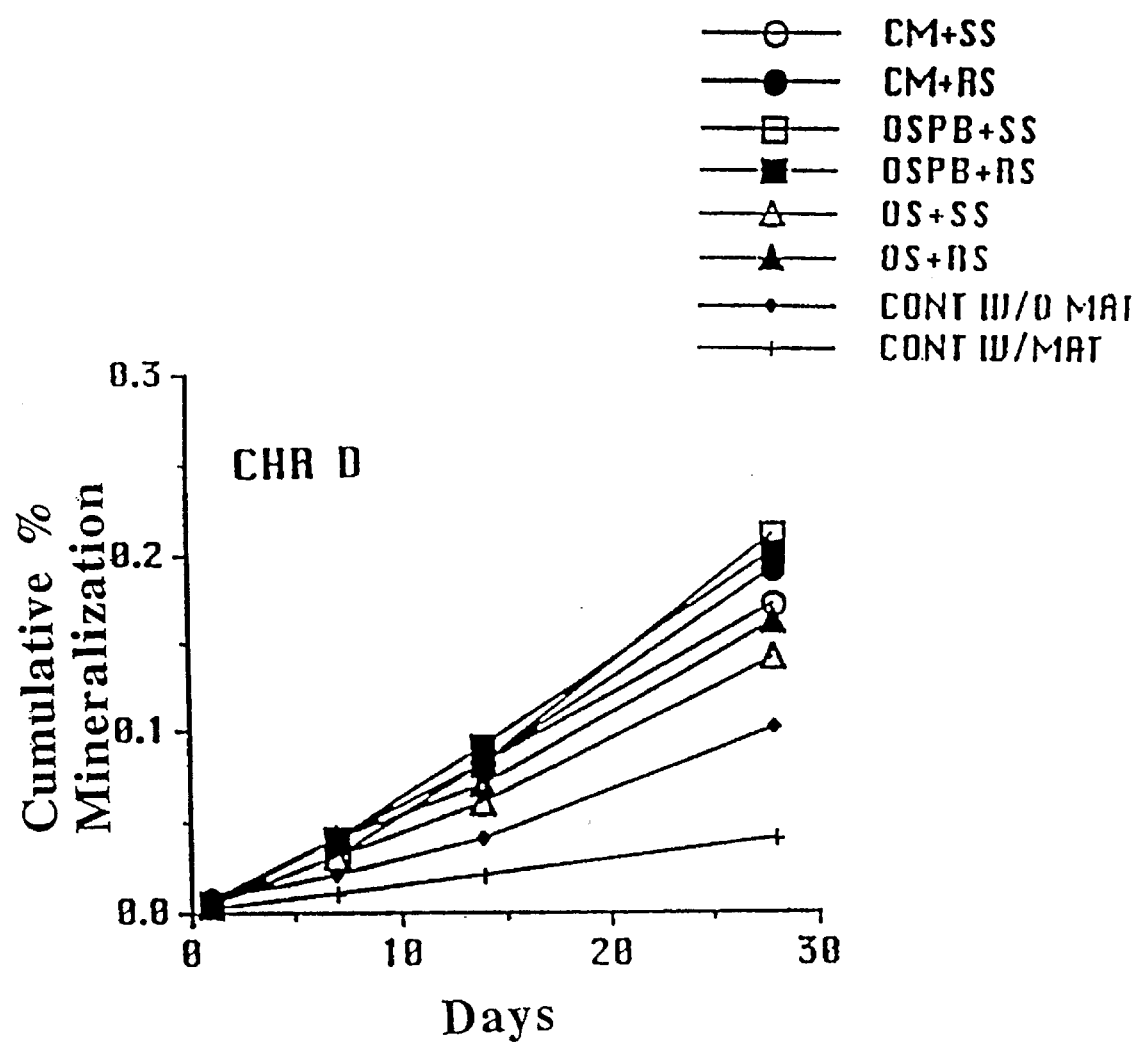
FIG. 4D shows different mat combinations with chrysene under dark conditions.

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

The invention will best be understood from the following experiments.

Three categories of microbes were used in the mat construction and s/x types of constructed mats were tested for their comparative capabilities of mineralizing hexadecane, a paraffin, and chrysene, a four ring polycyclic aromatic hydrocarbon (PAH).

Six treatments, or microbial mat types, were used. These included our laboratory-developed metal tolerant mats, as well as specifically constructed silage-microbial mats. The microbial groups used for constructed mats and their major characteristics were:

1. Oscillatoria spp.:
   Oxygenic phototrophic with heterotrophic ability.
   Nitrogen-fixing.
   Slime-generating.
2. Chromatium spp.:
   Anoxygenic phototrophic.
   Chemotropic.
   Motile, seeking low oxygen zones, penetrating soils.
   Raise redox by removing $H_2S$.
3. Fermentative anaerobic group, including
   Lactobacillus spp. and Clostridium spp. (from ensiled grass clippings or silage):
   Heterofermentative, using a variety of substrates including recalcitrant carbohydrates such as hemicellulose.

The mat construction process involved inoculating single isolates (or mixtures if fermentative bacteria) of the three microbial groups into sterile flasks with ensiled grass clippings. As mats matured the Chromatium spp. migrated under the Oscillatoda spp. and could be seen as red colonized areas. Grass clippings continued to degrade, indicating the presence of hemicellulose-degrading bacteria.

After all mats had matured into stable communities, which were tightly annealed in a gelatinous matrix, they were applied in non-sterile conditions to the petroleum distillate solutions. No attempt was made thereafter to protect the mat from invasion of wild microbes. However, they appeared to remain intact, maintaining the integrity of their microbial populations throughout the experiment.

Metal-tolerant and constructed silage-microbial mats

1. CM+SS; Complete mat (CM) and sterile silage (SS):
   These mats contained cyanobacteria (predominantly Oscillatoria spp.) and various species of bacteria, including purple sulfur photosynthetic bacteria. All of these species of cyanobacteria and bacteria emerged spontaneously from Georgia Piedmont Soil and have been previously adapted for metal tolerance (Bi, Cd, Co, Cr, Cu, Mn, Pb, Se, Zn) using know techniques.
   Silage provided organic acids (carbohydrates), bacteria and structural support for microbial mat attachment and development. In this mat type, the silage was autoclaved (SS) to remove the effect of the silage bacteria.
2. CM+RS; Complete mat and raw silage (RS):
   These mats contain the same soil microorganisms adapted for metal tolerance as No. 1 in addition to non-sterile, or raw, silage. Therefore, silage bacteria were present.
3. OSPB+SS; Oscillatoria spp. (OS), Chromatium spp. (PB and sterile silage:
   These mats contain commercially obtained Oscillatoria spp. and Chromatium spp. Autoclaved silage was added.
4. OSPB+RS; Oscillatoria spp., Chromatium spp. and raw silage:
   These mats contain the same microorganisms as No. 3 in addition to non-sterile silage. Therefore, silage bacteria were present.
5. OS+SS; Oscillatoria spp. and sterile silage:
   These mats contained only the Oscillatoria spp. as used in Nos. 4 and 5, in addition to sterile silage.
6. OS+RS; Oscillatoria spp. and raw silage:
   These mats contain only the Oscillatoria spp. as used in Nos. 4 and 5, in addition to raw silage.

These codes are used to identify the various mats in the figures.

A similar series of test tubes were set up to test the mineralization capabilities of only purple sulfur photosynthetic bacterium, Chromatium spp., a major component of microbial mats.

The following petroleum hydrocarbons were tested with each of the above mats:
   Hexadecane, a straight-chain alkane, and
   chrysene, a high molecular weight polycyclic aromatic hydrocarbon (PAH), were selected as representative constituents of petroleum. Both hydrocarbons were either $^{14}C$-labelled (chrysene: specific activity=6.3 mCi/mmol, Amersham Corp., Arlington Heights, Ill., and hexadecane: specific activity=1.2 mCi/mmol, Sigma Chemical Co., St. Louis, Mo.) or unlabelled.

The Experimental Design

Microbial mats contain both photosynthesizing and heterotrophic microorganisms, both of which could be capable of degrading the petroleum hydrocarbons. Some of the photosynthesizers also are effective heterotrophs. Therefore, the experimental design included a lighted and a dark series for each treatment (mat type) in an attempt to isolate differences in mineralization due to the provision of lack of light.

A total of 104 test tubes were used for all of the six mat types under lighted and dark regimens. These included: triplicate experimental tubes (with a live mat plug) for each mat type; one additional tube containing the $^{14}C$-labelled compound plus 25 mg/L of unlabelled chrysene or hexadecane for each mat type; one control tube without mat and spiked with the $^{14}C$-labelled compound for each hydrocarbon types; and one controlled tube with a microbial mat killed with 1 mL of 0.1M $HgCl_2$ and spiked with the $^{14}C$-labelled compound for each hydrocarbon type.

An additional 12 test tubes were used to test the mineralizing capabilities of Chromatium spp. One milliliter of the pure culture was used to set up a series in the same fashion as the microbial mat series.

Tests for significant differences in degradation among constructed mat treatments were performed using one-way analysis of variance and protected t-tests (GB-Strat Professional Statistics and Graphics, Dynamic Microsystems, Inc., Silver Springs, Md.).

Only one hydrocarbon was added to each tube. Additions of the $^{14}C$-labelled compounds to the test tubes were intended to spike the media at a level greater than 4800 dpm/mL. Therefore, each tube was spiked with 144,000 dpm/mL of $^{14}C$-labelled hexadecane (=12.259 up) or chrysene (=2.348 ug). In tubes containing an additional 25 mg/L of hydrocarbon, this amounted to an additional 375 uL of hexadecane or 375 ug of chrysene dissolved in methylene chloride.

Procedure

Pieces of microbial mat were separated, weighed (wet weight) and added to sterile borosilicate test tubes. One milliliter of chromatium spp. culture was added to its respective tubes. The appropriate $^{14}$C-labelled or unlabelled hydrocarbon was added and final tube volumes were adjusted to 15 mL through the addition of Allen/Arnon Modified Media (Allen & Arnon, 1955).

A 7-mL scintillation vial KOH trap containing 1 mL of 0.3M KOH was suspended inside each tube over the surface of the media using a piece of teflon tape. This latter was held firmly in place by a teflon tape-coated cork stopper. Teflon does not react with hydrocarbons (Bauer & Capone, 1985).

Lighted tubes were held under 24-h mixed fluorescent and incandescent lighting. "Dark" tubes were kept in the same location and covered with two layers of aluminum foil. Ambient temperature ranged from 28°–32° C.

Samples of the radioactive tube culture media (1 mL) were drawn and placed into a 7-mL scintillation vial at 0 and 28 days. At 1, 7, 14 and 28 days, the KOH trap from each flask was removed (and replaced at 1, 7, 14 days). Five mL of scintillation fluid (Ultima Gold, Packard Chemical Co., Meriden, Conn.) were added to each scintillation vial and counted for 10 minutes on a liquid scintillation counter (Packard Bell). At Day 28, the pH of each test tube media was lowered to <4.5 with $H_2SO_4$ in order to drive $CO_2$ from the media and into the KOH trap.

Hexane was used to wash $^{14}CO_2$ from selected microbial mat samples. These were scintillation counted to obtain gross information on $^{14}C$ incorporation.

Results

Results are reported separately for each mat of the six mat types over the 28-day period as follows: KOH trap $^{14}C$-levels in dpm/mL and normalized for the initial microbial mat weight (FIG. 1); normalized KOH trap dpm/mL values converted to ng of hydrocarbon mineralized in ng/h (for the first 24 hours) or ng/day (FIGS. 2 and 3); and the mineralization rate calculated as a percentage of the initial amount of hydrocarbon spiked into each tube (FIG. 4). Chromatium spp. mineralization is presented in Table 1.

Neither the $^{14}C$-labelled hexadecane or chrysene, nor tubes containing an additional 25 mg/L of hexadecane or chrysene as toxic to the microbial mat. Under lighted conditions, mat wet weight increased an average of 103.3% (s.d.=68.4 over the treatment means) in hexadecane and 140.6% (s.d.=107.0 over the treatment means) in chrysene. Mat wet weights generally increased little, or even decreased, under dark conditions in hexadecane (mean=−7.2%, s.d.=47.3 over the treatment means) and chrysene (mean=26.0%, s.d.=25.7 over the treatment means).

Despite the intended spiking rate of >4800 dpm/mL, hexadecane showed lower counts in the 1-mL media samples drawn at the moment of initial spiking (lighted series mean=755.01 dpm/mL, s.d.=354.90; and dark series mean=2803.38 dpm/mL, s.d.=658.60). The initial counts of the CM+RS treatment compared to all other treatments, while under dark conditions, OSPB+RS treatment showed the greatest degradation (significant at p<0.01 or 0.05 compared to CM+SS, OS+SS and OS+RS). With chrysene, degradation in lighted and dark conditions followed the same trend (CM+RS mat under light; OSPB+RS mat in dark), though these results were not statistically significant. All Oscillatoria spp. treatments (OS+RS and OS+SS) had the lowest counts of all (except OS+RS Hex L). When an additional 25 mg/L of unlabelled hydrocarbon was added as excess nutrients to the test tube media, $^{14}CO_2$ counts were usually lower, but the same general trends persisted (data not shown).

Mineralization rate calculations parallel $^{14}CO_2$ values. The mineralization rates were more than 150-fold greater for hexadecane compared to chrysene during the first 24 hours. Examining the dark series data, for both hexadecane and chrysene, the rate of mineralization steadily increased through the four-week experiment. During this time, hexadecane was degrading at a rate >400-fold over chrysene. During the first 24 hours, experimental values ranged from 0.01–0.04 ng/h for chrysene lighted series to 1.5–12.2 ng/h for hexadecane lighted series. Dark series values for the same time period ranged from 0.01–0.10 ng/h for chrysene and 3.0–27.6 ng/h for hexadecane. Daily mineralization rates, by Day 28 ranged from 0.022–0.644 ng/day in the chrysene lighted series to 3.6–100.4 ng/day in the hexadecane lighted series. Dark series values for the same time period ranged from 0.494–2.998 ng/day for chrysene and 63.2–1232.8 ng/day for hexadecane.

During 28 days, the percent mineralization of the entire originally spiked amount was significantly greater for hexadecane compared to chrysene (FIG. 4). Final lighted series experimental values ranged from 0.01–0.08% for chrysene and 0.47–3.07% for hexadecane. Final dark series experimental values ranged from 0.14–0.21% for chrysene and 4.65–14.29% for hexadecane.

At Day 28, hexane-washed samples of mat were examined for evidence of incorporation into microbial mat biomass of $^{14}CO_2$ generated by the mineralization of hexadecane or chrysene. High levels of $^{14}CO_2$ were detected in all samples (Table 2). Chromatium spp. also degraded hexadecane and chrysene similarly under lighted and dark conditions (Table 2). Hexadecane was again degraded at a much greater rate than chrysene.

While there is some information to suggest the potential for cyanobacterial degradation of hydrocarbons, these experiments show that a constructed mat having chemotrophic bacteria in combination with a cynobacteria and fermentative bacteria produce superior results in mineralization. By the end of the experiment, it was notable that the addition of silage and its accompanying microbial flora (raw silage contains Lactobacillus spp. and Clostridium spp.) usually significantly enhanced hydrocarbon mineralization. The most effective mineralizers of both hexadecane and chrysene under lighted conditions were the complete mats developed from naturally-occurring microorganisms (predominately Oscillatoria spp. and purple sulfur photosynthetic bacteria from Georgia Piedmont soil). Without the interference of $^{14}CO_2$ uptake via photosynthesis, the dark experimental series are the most reliable data. Under this latter scenario, the constructed mat of commercially purchased Oscillatoria spp. and Chromatium spp. was the most effective mineralizer of both hexadecane and chrysene.

There is substantial evidence that several microbial species in a mixed culture may be necessary for significant oil degradation, since no single species appears to be able to completely degrade a particular oil. Our results clearly suggest that microbial mats dominated by cyanobacteria and also populated by a chemotrophic bacteria have bioremediation potential for petroleum.

Figure 5:
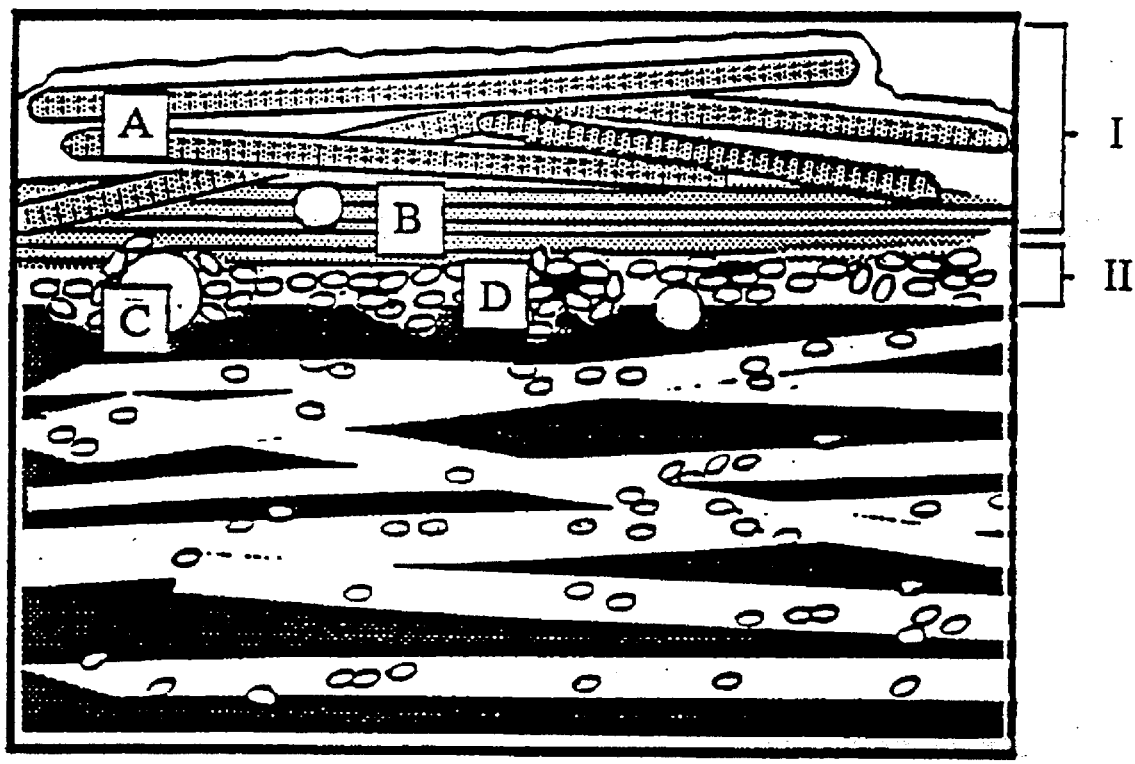
FIG. 5 is a schematic representation of a microbial mat.

We have found that our silage-microbial mats tolerate hypersaline conditions (up to 100 parts per thousand) with no pre-adaptation. In another parallel series of stepwise adaptation experiments, we found silage-microbial mats survived in variable concentrations of naphthalene and phenanthrene to 100 mg/L, chrysene to 50 mg/L and pure hexadecane. Each of our microbial mats is a consortium containing Chromatium sp., a purple, autotrophic/ chemotrophic bacterium and Oscillatoda sp., a photosynthetic/nitrogen-fixing cyanobacterium. The floating mat on the surface of water is stabilized and nitrified by ensiled grass clippings schematically shown in FIG. 5. Zone 1 is dominated by photosynthetic/nitrogen-fixing cyanobacterium Oscillatoria and zone 2 is dominated by heterotrophic/chemotrophic and autrophic/chemotrophic bacteria Chromatium. The Osciilatoria is indicated in FIG. 5 by A, the ensiled grass clippings are indicated by B, air bubbles contributing to mat buoyancy are indicated by C, and the heterotrophic or autotrophic bacteria Chromatium is indicated by D.

Figure 6:
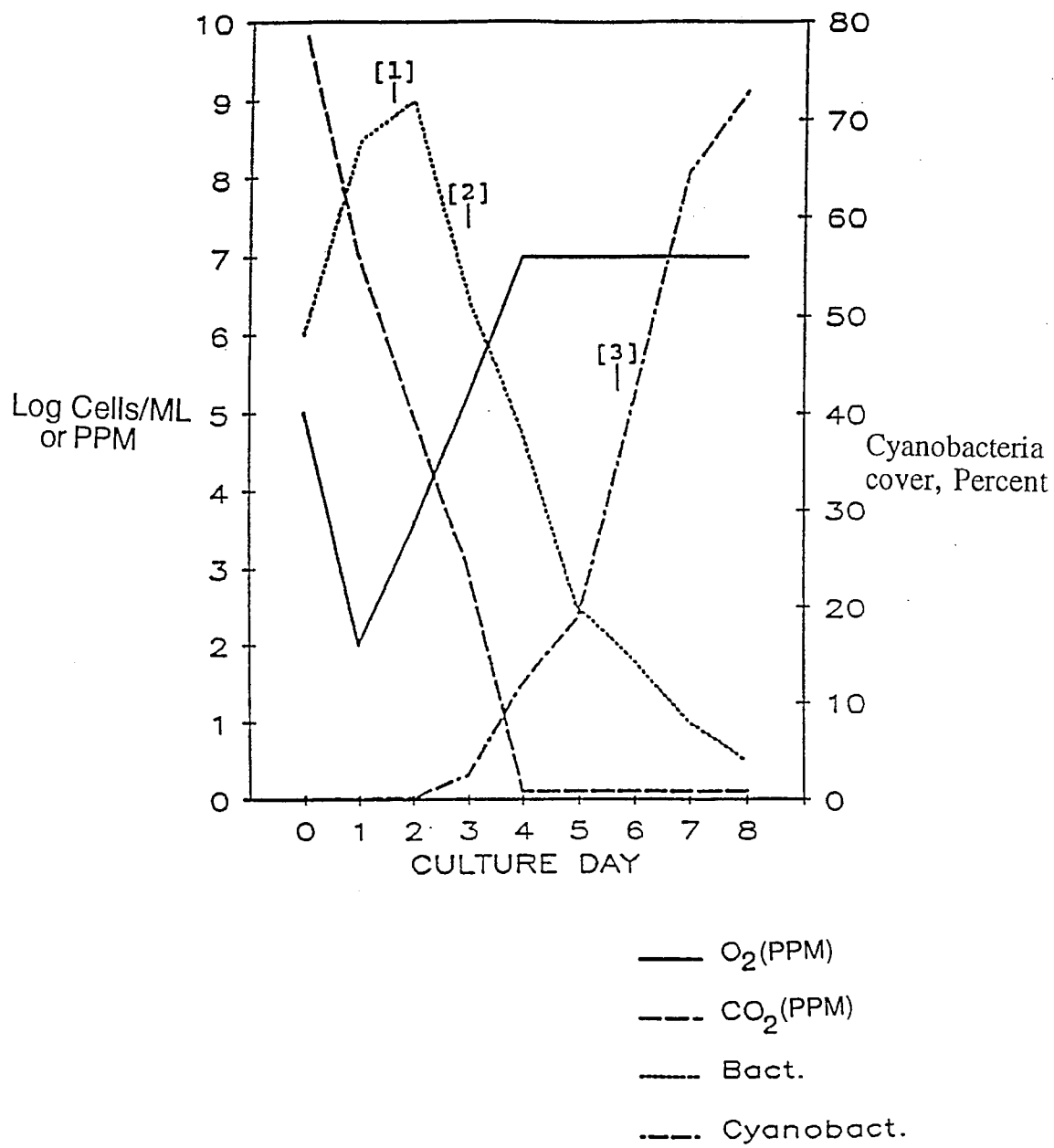
FIG. 6 graphically depicts the correlation of Cyanobacteria growth with decreasing populations of bacteria in the water column.

The water is inoculated with our laboratory stocks or commercial sources of Chromatium and Oscillatoria. Our stocks are resilient, durable strains, which have been pre-adapted to tolerant a number of toxic chemicals and metals. FIG. 6 illustrates a predictable succession of microbes that occurs in the water column when this mat consortium is developed in water lying over an optional soil bed. Initially there is a bloom of a wide variety of heterotrophic bacteria (1–3 days) emerging from the soil bed, followed by a rapid colonization of the water column surface by Oscillatoria. As the Oscillatoria grows, the bacteria in the water column disappears. The Chromatium migrates to the region under the Oscillatoria, where it is supported by carbohydrates and proteins supplied by the cyanobacteria. However, Chromatium retains its mobility and part of the population often migrates away from Oscillatoria through the water or soil below the mat. The former are, however, unable to sustain their viability for extended periods away from the mat without the addition of nutritional supplements. As necessary, mature mats are adapted to the target contaminants by step-wise exposure to increasing concentrations of the contaminant.

It is important to note that Chromatium is a chemotrophic organism (metabolizes a variety of chemicals for energy). Although it is also autotrophic (photosynthetic), photosynthesis does not limit its chemotrophic responses. It is a unique, primitive organism which uses $H_2S$ instead of water for photosynthesis. This sequester of sulfide from water with subsequent oxidation to elemental sulfur removes some of the reducing potential of the environment and probably contributes to the elevated redox conditions that exist around mats.

Mature mats become tightly annealed in a slimy matrix, secreted by the cells. The resulting laminated sheets of microbes have discrete oxidizing and reducing zones lying in close proximity within the matrix. These characteristics (availability of oxidizing/reducing zones, and elevated redox conditions in the water column) likely contribute to the removal of various metals from water.

Mats are easily immobilized on a variety of substrates including; glass wool, ceramic tiles, limestone pebbles, concrete and filamentous green algae. When immobilized on green algae, they are effectively protected from grazing in the field environment (mechanism unknown). Ponds containing mats immobilized on green algae have persisted in field ponds for six months.

Microbial mats have a unique ability to actively sequester chlordane globules from the bottom of the water column via biofilms. For example, a biofilm has progressively extended toward the bottom of test tubes containing various concentrations of hexadecane. This film has demonstrated that it can sequester chlordane globules many times its own weight. This characteristic may be important to the removal of dense contaminants, which fall to the bottom and pollute the sediment regions of shallow ponds and estuaries.

Production of mats

The following steps summarize the procedures for producing microbial mats:

1. Add ensiled grass clippings (7 g/L) made from fresh-cut grass clippings (mixed wild grasses) that are packed into 1-liter jars, excluding air pockets, and allowed to process anaerobically for 20 days at room temperature, to the surface of a water column and Oscillatoria/Chromatium mixture (0.1–0.5 g/L each). The finished silage is used to enrich the water column in order to stimulate the microbial bloom and provide a substrate for cyanobacteria attachment at the surface of the water column. There is no attempt to maintain a sterile system or to control the types of heterotrophic bacteria that may integrate with the mat. Two microbial strains are considered as essential to the treatment system. These are Oscillatoria and Chromatium. Each of these easily colonizes on the grass clippings and are not eliminated by competitive interferences of other heterotrophs. Additionally, a mixed population of fermentative bacteria are added with the ensiled grass clippings. It is assumed that the mixed heterotrophic populations from the soil and grass clippings may actually enhance degradation of certain compounds as long as the two inoculated strains retain their integrity. In summary, after the inoculation of the two strains, there is a natural, balanced self-organization of the microbes into a mat dominated by Oscillatoria with persistent Chromatium on the underside of the mat. This self-organization and long-term structural durability of the system is highly reproducible.
2. Illuminate with incandescent lights (60 watt at 25 cm from surface). Partially cover with clear plastic to minimize evaporation.
3. Bacterial phase develops spontaneously (1–3 days).
4. Cyanobacteria spontaneously establishes dominance in 4–7 days. Allow mat 10–15 days to mature. Replace evaporated water with tap water. Microbial mats tolerate tap water, and fresh and brackish water from the field environment. Saline water may be used after pre-adaptation (step-wise exposures) of the strains to increasing salt concentrations.
5. Thereafter use excised sections of mature mat for microbial inoculum (1–2 $cm^2$/L water).

Application of the Mat in Bioremediation

Figure 7:
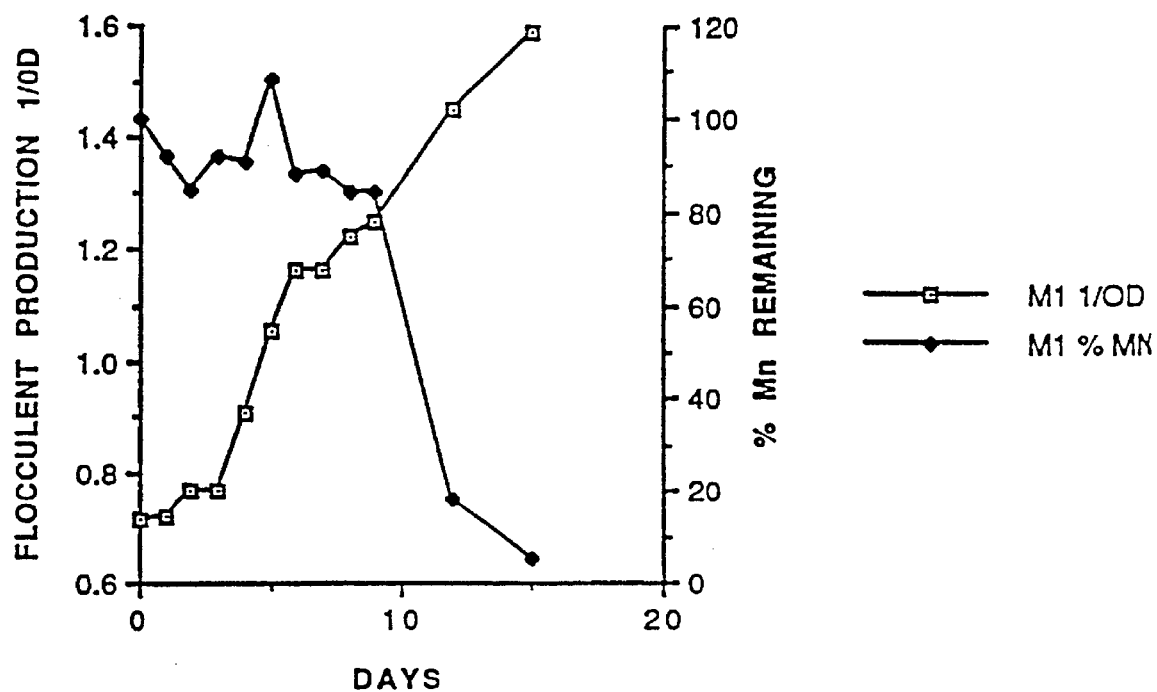
FIG. 7 illustrates bioflocculant production and manganese removal from contaminated water. Percent metal remaining in solution is plotted. 1/OD measures flocculating activity. M1 contained an initial manganese concentration of 20 mg/L.

Microbial mats exhibit a number of characteristics that can be applied to simple wastewater treatments. These properties include the following: (1) production of flocculents that clarify the water column of turbidity as seen in FIG. 7, (2) sequester of eutrophying minerals, (3) elevation of acidic pH levels (Table 1), (4) degradation of organic materials and (5) removal of heterotrophic bacteria (including coliforms) from the water column. FIG. 6 illustrates that the decrease in the water column bacteria correlates with the growth of Oscillatoria on the pond surface.

TABLE 1

Aqueous pH changes mediated by microbial mats over time.

| Day | Triplicate Mean pH |
|---|---|
| 1 | 5.20 |
| 2 | 6.52 |
| 3 | 6.94 |
| 4 | 7.20 |
| 5 | 7.79 |

TABLE 1-continued

Aqueous pH changes mediated by microbial mats over time.

| Day | Triplicate Mean pH |
|-----|--------------------|
| 6   | 8.29               |
| 7   | 8.80               |
| 8   | 9.25               |
| 9   | 9.83               |
| 10  | 10.14              |
| 11  | 10.34              |

Figure 8:
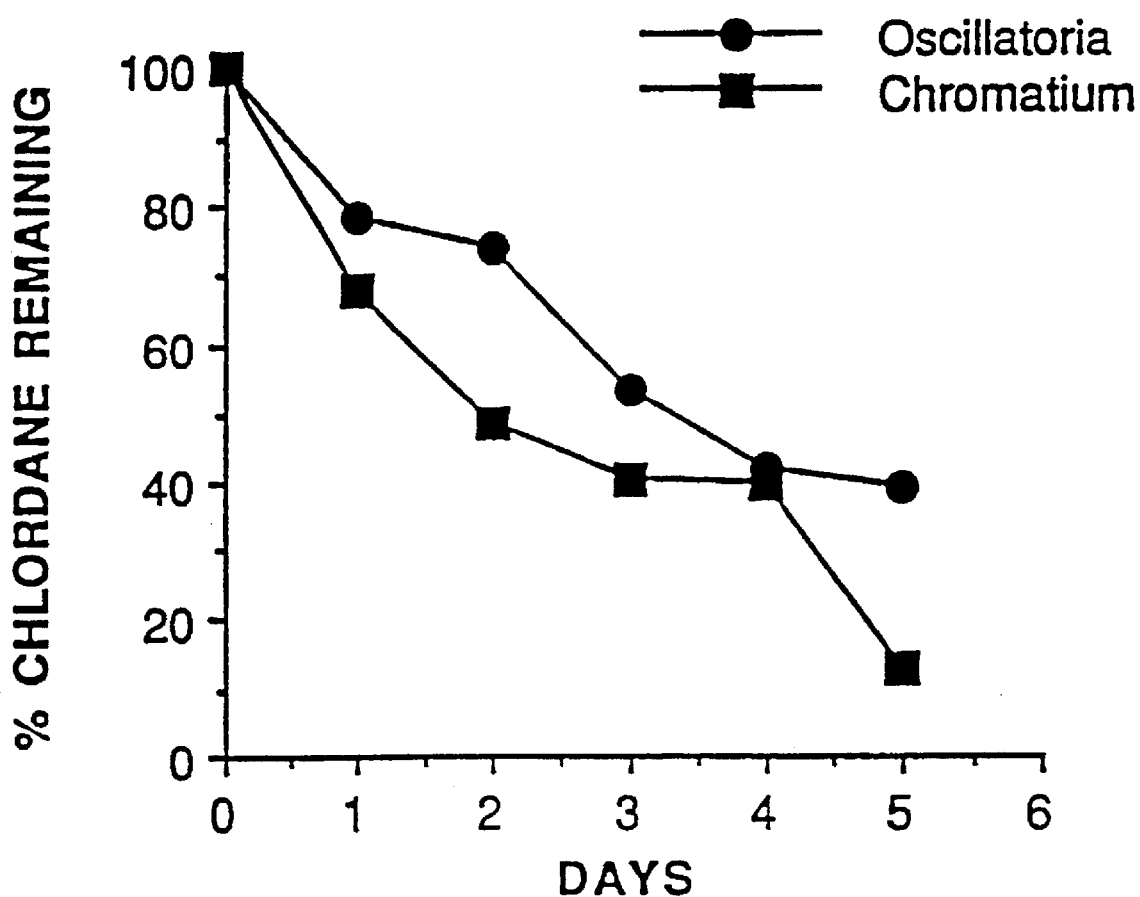
FIG. 8 graphically depicts the removal of chlordane by Oscillatoria and Chromatium..
Figure 9A:
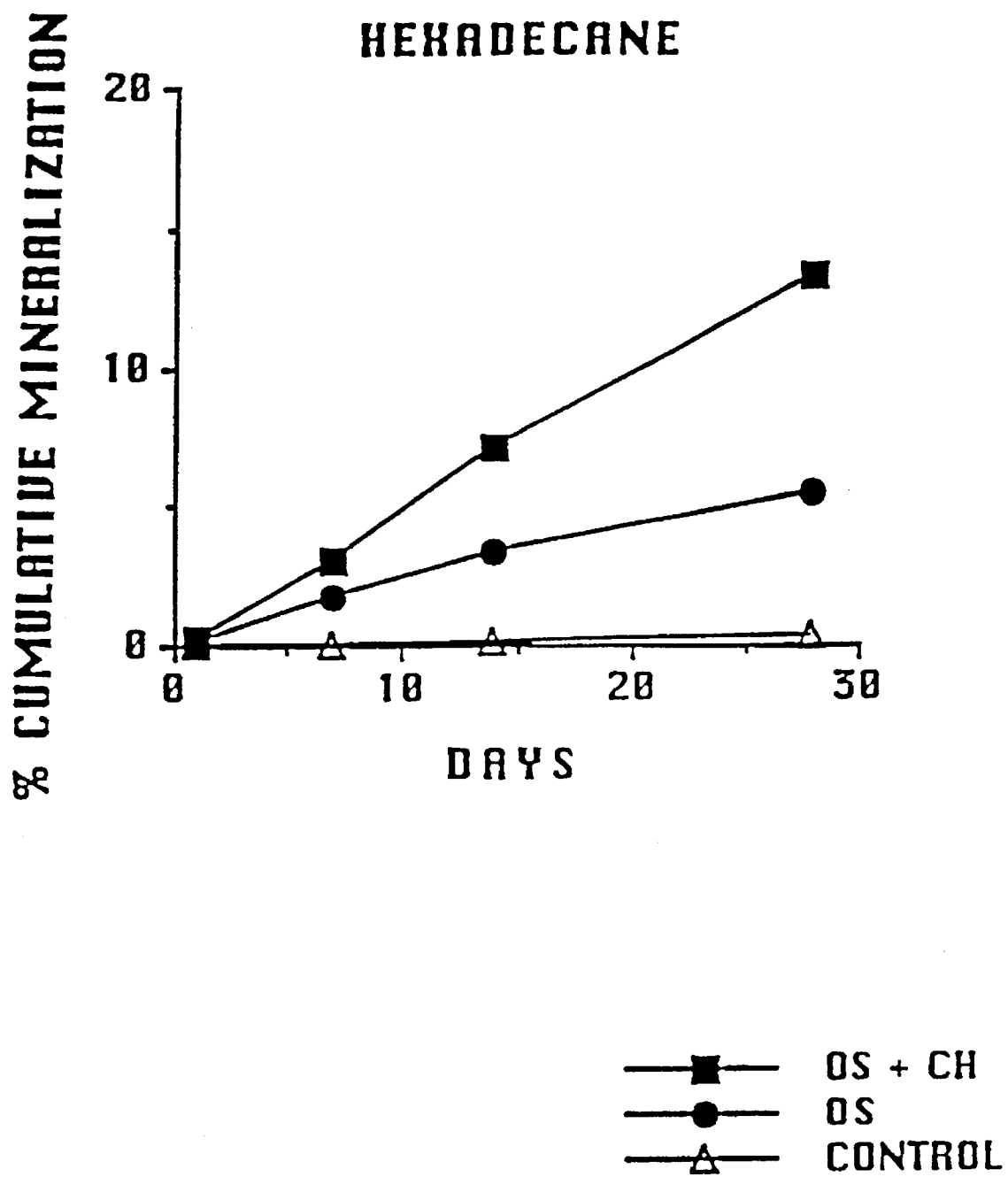
FIG. 9A graphically depicts the percent cumulative mineralization of hexadecane.
Figure 9B:
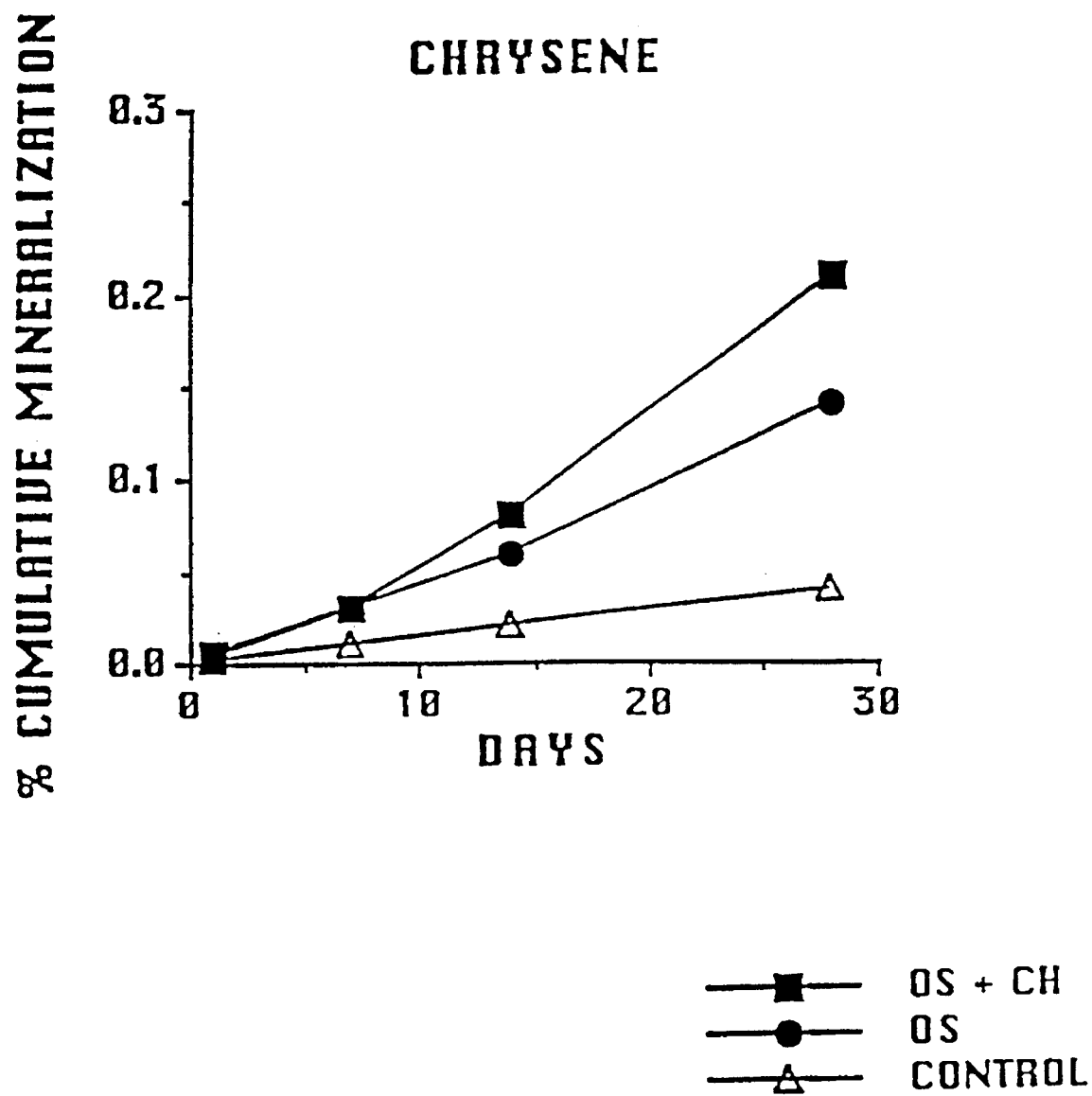
FIG. 9B graphically depicts the percent cumulative mineralization of chrysene. OS+CH is Oscillatoria and Chromatium consortium: OS is Oscillatoria done.
Figure 10:
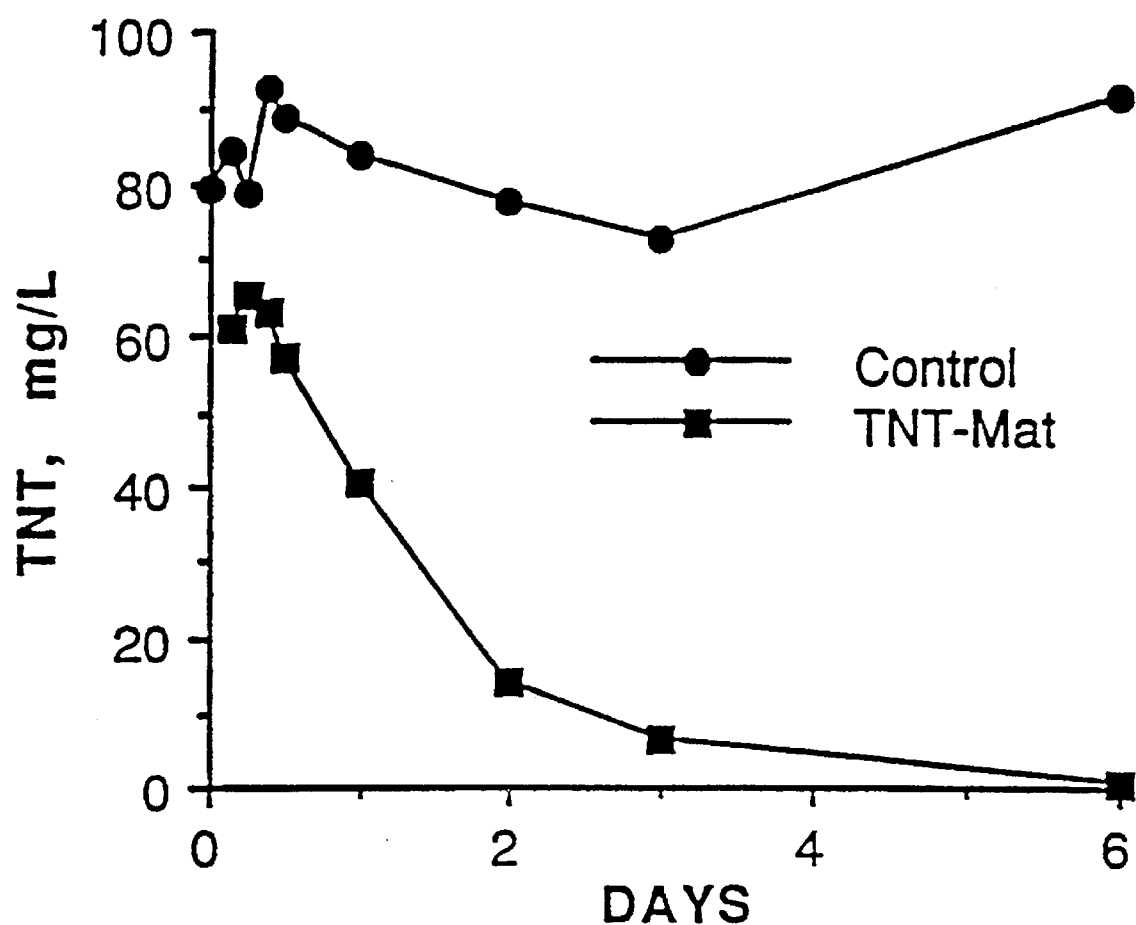
FIG. 10 graphically depicts the degradation of 2,4,6-trinitrotoluene (TNT) by a mat.
Figure 11A:
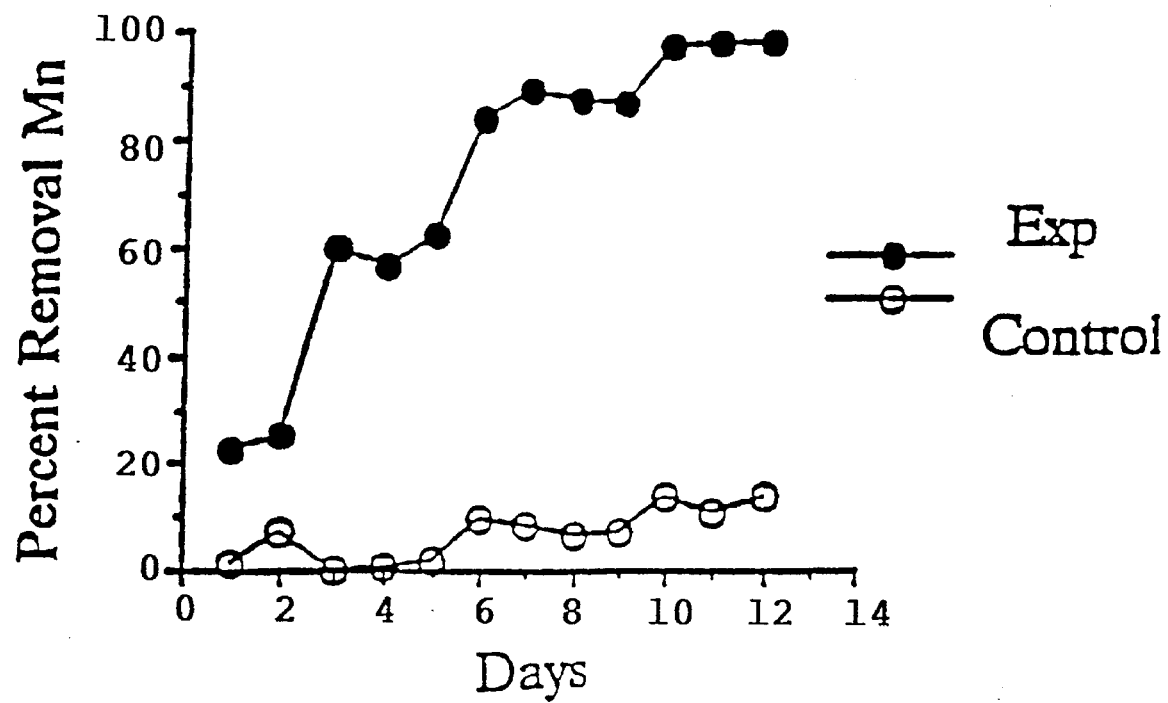
FIG. 11A graphically depicts the removal of manganese from solution by mat floaters.
Figure 11B:
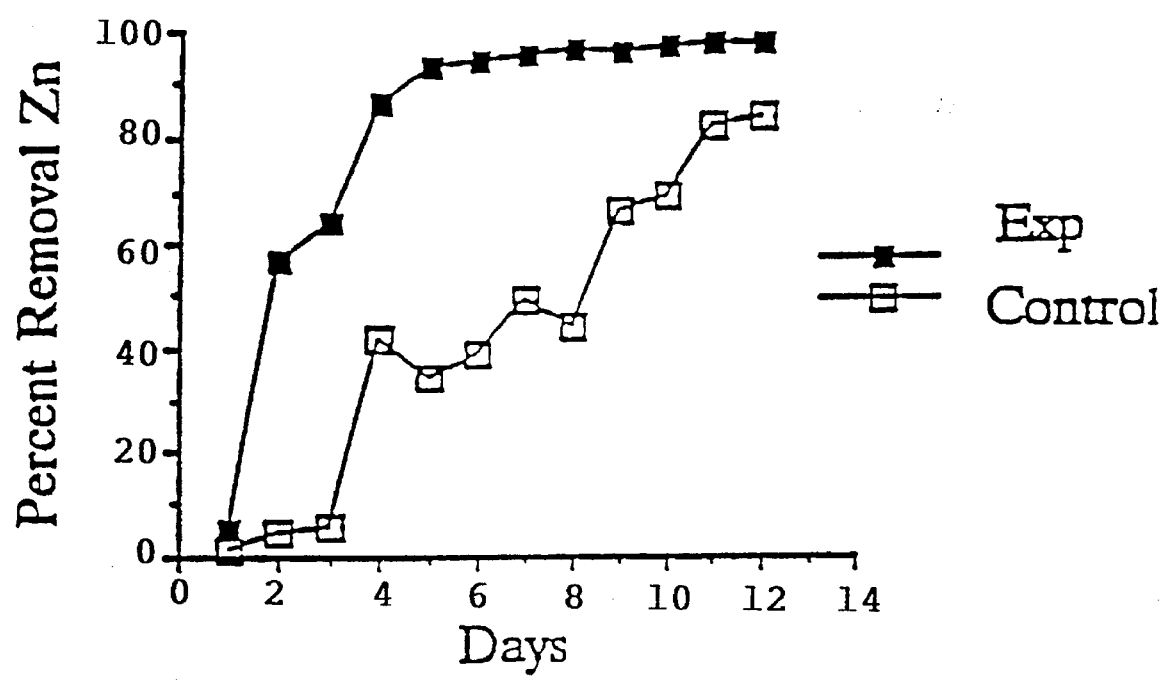
FIG. 11B graphically depicts the removal of zinc from solution by mat floaters.

Mats have successfully been used to degrade chlordane, hexadecane, chrysene, naphthalene, phenanthrene, 2, 4, 6-trinitrotoluene (TNT) and poly-chlorinated biphenyl (PCB). Representative data is presented in FIGS. 8–10 and Table 2. Chlordane in water degradation data demonstrates that Chromatium degrades at a faster rate than Oscillatoria. Chlordane in soil is also rapidly degraded by the microbial mat. There is an intense Chromatium bloom in water with chlordane. A similar phenomenon of red Chromatium penetration in soil was observed. In the example of hexadecane and chrysene, complete mineralization to carbon dioxide occurs with Oscillatoda but is significantly enhanced when Chromatium is present with in a mat with Oscillatoria. TNT is degraded with the complete mat.

TABLE 2

Biodegradation by microbial mats.

| Contaminant | Concentrations, mg/L Initial | Concentrations, mg/L Final | Time and percent degradation |
|-------------|---------|---------|----------------------|
| Chlordane   |         |         |                      |
| in water    | 2,100   | 61      | 97% in 10 days       |
| in soil     | 200     | 146     | 27% in 25 days       |
| Petroleum distillates[(1)] |  |   |                      |
| hexadecane  | 768     | 697     | 9% in 90 days        |
| phenanthrene| 374     | 284     | 24% in 90 days       |
| chrysene    | 157     | 125     | 20% in 90 days       |
| 2,4,6-trinitrotoluene (TNT) | 100 | <1 | >99% in 6 days |
| PCB         | 100     | EIP[(2)]| 50% in 5 days        |

[(1)]Percent degradation for petroleum distillates designate mineralization in dark cycle experiments (determined by $^{14}$C-labeled carbon dioxide collected in potassium hydroxide traps). Quantity of mat (mat surface area, cm$^2$) applied to the various substrates were: TNT = 2.0 per petri plate, chlordane in water = 16.0 per 50-ml media, chlordane in soil = 2.5 per test tube, petroleum distillates = 2.0 per 100-mL media.
[(2)]EIP: Experiment in progress.

Table 3 presents a summary of the metal removal capacity of the mats. Although cell sorption by cyanobacteria and bacteria has long been known as a process of removing metals from aqueous media, the mat system operates with a unique set of mechanisms. Mediation of the chemical environment of the water column under the mat is likely involved in the process. High redox conditions (present also in the dark) and high oxygen during the day likely deposits Mn as $MnO_2$. Micro-analysis of mats exposed to zinc (Zn) and manganese (Mn) show little congruency of the metal deposits with cell morphology (indicating that cell sorption may not be the primary mechanism of metal deposit, rather it is the aforementioned mediation of the local chemical environment).

TABLE 3

Metal and metalloid removal is quiescent laboratory ponds.
Pb = lead, Se = selenium, As = arsenic,
Zn—zinc, Mn = manganese, Cu = copper, Cd = cadmium.

| Treatment system | Initial concentration, mg/L | | Removal rate, mg metal/m$^2$ mat/h |
|---|---|---|---|
| Free floating mats[(1)] | Pb: | 117 | 129 |
|  | Se: | 37 | 6 |
|  | As: | 100 | RND[(s)] |
| Mat immobilized on floaters[(3)] | Mix of |  |  |
|  | Zn: | 22 | 313 |
|  | Mn: | 18 | 462 |
| Excised mats[(4)] | Mix of |  |  |
|  | Cu: | 284 | 378 |
|  | Zn: | 3,021 | 3,778 |
|  | Cd: | 19 | 356 |

[(1)]Free floating mat. Self-buoyant mats were cultured on the surface of laboratory ponds containing lead (Pb) or selenium (Se). Initial solution of selenate was reduced in part to elemental selenium which deposited in the surface mat. Pb was deposited in the mat as lead sulfide. The pH conditions for the free floating mats was 6–8.
[(2)]RND. Rate not determined. 1,746 mg As/M$^2$ was removed by day 19. Interim samples of the water column were not taken.
[(3)]Mat immobilized on floaters. Mat was attached to glass wool balls which were floated in Zn/Mn-contaminated water at pH 7–9.
[(4)]Excised mats. Small sections of mat were excised and applied to a mixed solution of Cu, Zn, Cd and iron (Fe) sample from Iron Mountain Mine drainage in California. The pH was adjusted to 3–4 before adding mat sections. Fe was not measured.

Figure 12:
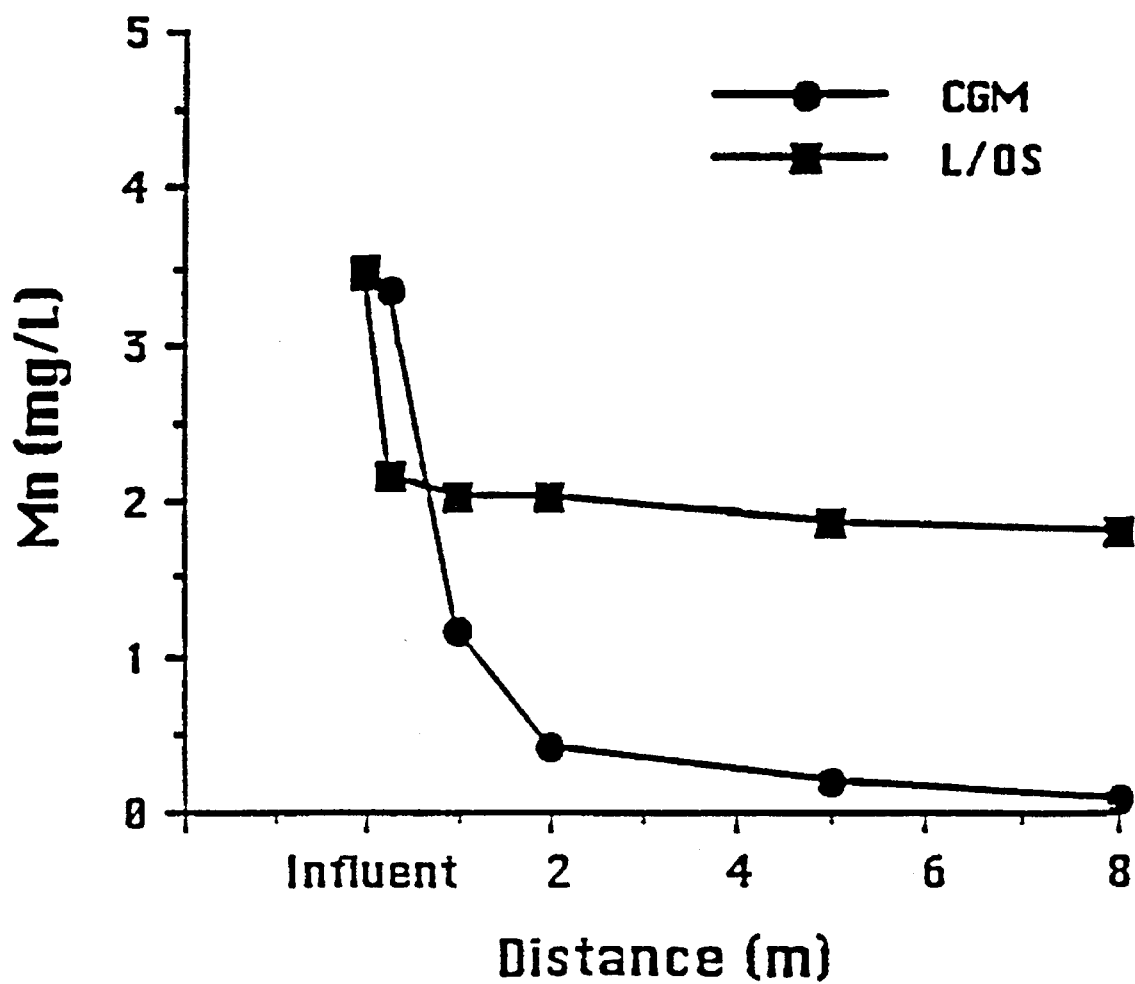
FIG. 12 graphically depicts the removal of manganese from a continuous flow of acid-mine drainage. CGM is a microbial mat/green algae pond. L/OS limestone substrate with a cover of Oscillatoria pond.

In a field pond application of microbial mats in the sequester of metal-contaminated mining water, a floating mat (1–2 cm thick), composed of Oscillatoria, immobilized on filamentous green algae, grew rapidly in the pond after addition of silage-microbial mat inocula. A secondary mat of cyanobacteria also covered the limestone at the bottom. Thus the metal-contaminated water flowed between the double-layered mats. Approximately six weeks were required to establish a full pond mat cover, but effective metal removal began in the early stages of mat growth. FIG. 12 shows the metal removal profiles in the ponds at flow rates of 2–5 L/min. Metals (Mn and Fe) were effectively removed after the inflow water had flowed a distance of approximately 1–2 m through the pond. All sampling points beyond that distance showed metal concentrations <1,2 mg/L. Patches of red colonies indicated the presence of Chromatium in and around the mat. There is no evidence of metal deposit on the top surface of the mat. High redox conditions in the water column, mediated by the photosynthetic processes of these two microbial groups, likely resulted in the rapid deposit of the Mn. It has remained functional for 5 months in depositing approximately 2.6 g of Mn/M$^2$/day.

Redox and dissolved oxygen levels were high during the light period and pH levels ranged from 6.4–7.7. Even after 10 h of darkness, oxygen levels remained at 6 mg/L in some regions of the mat pond. During the photosynthetic period bubbles of oxygen become entrappeal in the slimy matrix that typically binds the mat. Apparently this sequestered oxygen remains available throughout the night. This is to be expected since cyanobacteria are unusual in that they have limited ability to utilize organic substrates for energy production in the dark, thus the oxygen consumption remained low.

Although the conditions of high oxygen and redox may be central to the deposit of Mn oxides, other factors may be functional as well. Flocculents were identified in the water column under the mat. Laboratory research showed that specific bioflocculents were released by the mat in response to the presence of $Mn^{+2}$ (manuscript in preparation). These materials carried surface charges ranging from −58.8 to −65.7 mV. The charges changed to +1.8 in the presence of divalent metal, indicating metal-binding to the bioflocculent.

Although metals which are adsorbed, precipitated or complexed can be released back into solution in an equilibrium response, no such fluctuations have been detected thus far during a four-month experimental period. Conditions of neutral pH with high dissolved oxygen and redox levels (mediated by the biochemistry of the mat ecosystem) favor the chemical precipitation of Mn oxides and Fe hydroxides. These, in turn, act as reservoirs for additional metal deposit.

The potential bioavailability of metals is favored by increases in acidity, reducing power and salinity. Constructed mats, containing Oscillatoria and Chromatium, would tend to lower bioavailability by raising the pH and redox of the system. Although anaerobic zones have been identified within the laboratory-cultured mats and are likely present in the field mat, the redox conditions of the water column under the mat is the experimental pond remained high even after extended dark periods.

Although only the chemotrophic bacteria Chromatium has been disclosed herein, any member of the family Chromatiaceae that has chemotrophic properties may be used without departing from the scope of the invention.

What is claimed as invention is:

1. A constructed microbial system comprising:
   a chemotrophic bacteria; and
   growing means for supplying said chemotrophic bacteria with exogenous protein and carbohydrate to sustain the growth of the chemotrophic bacteria.

2. The microbial system of claim 1 wherein said growing means includes cyanobacteria.

3. The microbial system of claim 2 wherein said growing means includes ensiled vegetation.

4. The microbial system of claim 3 including:
   a mat having been formed by inoculating said ensiled vegetation with said cyanobacteria and said chemotrophic bacteria and allowing said mat to grow from said inoculated ensiled vegetation.

5. The microbial system of claim 4 wherein said chemotrophic bacteria is of the genus Chromatium.

6. The microbial system of claim 5 wherein said cyanobacteria is of the genus Oscillatoria.

7. The microbial system of claim 1 further comprising:
   an immobilizing substrate carrying said chemotrophic bacteria and growing means.

8. The microbial system of claim 7 wherein said immobilizing substrate comprises a filamentous green algae.

9. The microbial system of claim 1 wherein said system will float on water.

10. A microbial mat adapted to overly the area to be treated comprising:
    an upper zone comprising dominately a photosynthetic cyanobacteria; and,
    a lower zone comprising dominately a chemotrophic bacteria and adapted to lie in contact with the area to be treated.

11. The microbial mat of claim 10 further comprising ensiled vegetation associated with said upper and lower zones to supply nutrients to said upper and lower zones.

12. A method of constructing a microbial mat comprising the steps of:
    a) inoculating ensiled vegetation with a chemotrophic bacteria and a cyanobacteria; and,
    b) allowing the ensiled vegetation, chemotrophic bacteria and cyanobacteria to grow into a mat.

* * * * *